(12) United States Patent
Carr et al.

(10) Patent No.: US 6,913,760 B2
(45) Date of Patent: Jul. 5, 2005

(54) DRUG DELIVERY COMPOSITION

(75) Inventors: Daniel B. Carr, Chestnut Hill, MA (US); Andrzej W. Lipkowski, Warsaw (PL); Donald L. Wise, Belmont, MA (US); Vasif Hasirci, Ankara (TR)

(73) Assignee: New England Medical Hospitals, Inc., Boston, MA (US)

( * ) Notice: Subject to any disclaimer, the term of this patent is extended or adjusted under 35 U.S.C. 154(b) by 0 days.

(21) Appl. No.: 10/213,584

(22) Filed: Aug. 6, 2002

(65) Prior Publication Data

US 2003/0170288 A1 Sep. 11, 2003

Related U.S. Application Data

(60) Provisional application No. 60/310,434, filed on Aug. 6, 2001.

(51) Int. Cl.[7] .................... A61E 13/00; A61E 2/00; A61K 9/14
(52) U.S. Cl. ............... 424/422; 424/423; 424/426; 424/428; 424/484; 424/485; 424/486
(58) Field of Search ................ 424/422, 423, 424/426, 428, 484–486

(56) References Cited

U.S. PATENT DOCUMENTS

| | | | | |
|---|---|---|---|---|
| 5,543,156 A | * | 8/1996 | Roorda et al. | 424/484 |
| 5,834,010 A | * | 11/1998 | Quan et al. | 424/448 |
| 6,605,294 B2 | * | 8/2003 | Sawhney | 424/426 |
| 2003/0068371 A1 | * | 4/2003 | Oshlack et al. | 424/465 |

OTHER PUBLICATIONS

Curley et al, Prolonged Regional Nerve Blockade, Jun. 1996, Anesthesiology, vol. 84 pp. 1401–1410.*
Ahmedzai, S., "Current strategies for pain control", Annals of Oncology, 8: 21–24, 1997.

Bennett, et al., "A peripheral mononeuropathy in rat produces disorders of pain sensation like those seen in man", Pain, 33(1): 87–107, 1988.

Carr, et al., "Spinal tube of analgesia: Opiods and future options", Neural Blockade in Clinical Anesthesia and Management of Pain, Cousins and Bridenbaugh, eds., 915–983, 1998.

Chary, et al., "The dose response relationship of controlled–release codeine (codeine contin) in chronic cancer pain", Journal of Pain and Symptom Management, 9(6): 363–371, 1994.

Cooper, et al., "Patient–controlled extradural analgesia to compare bupivacaine, fentanyl and bupivacaine with fentanyl in the treatment of postoperative pain", British Journal of Anaesthesia, 70: 503–507, 1993.

Curley, et al., "Prolonged regional nerve blockade", Anesthesiology, 84(6):1401–1410, 1996.

Dahm, et al., "Six years of continuous infusion of opioid and bupivacaine in the treatment of refractory pain due to intrapelvic extrusion of bone cement after total hip arthroplasty", Regional Anesthesia and Pain Medicine, 23(3): 315–319, 1998.

(Continued)

Primary Examiner—Alton Pryor
(74) Attorney, Agent, or Firm—Mintz, Levin, Cohn, Ferris, Glovsky and Popeo, P.C.; Ingrid A. Beattie, Esq.

(57) ABSTRACT

The invention provides a drug delivery compositions and methods for treating pain. A drug delivery composition contains a polymer and at least two drugs sucha as an analgesic agent and an anesthetic agent.

28 Claims, 6 Drawing Sheets

OTHER PUBLICATIONS

Dietz, et al., "Bupivacaine preferentially blocks ventral root axons in rats", Anesthesiology, 88: 172–180, 1997.

Fletcher, et al., "Antinociceptive effect of bupivacaine encapsulated in Poly(D,L)–Lactide –co–glycotide microspheres in the acute inflammatory pain model of carrageenin–injected rats", Anesthesia and Analgesia, B4(1) 90–94, 1997.

Grant, et al., "Prolonged analgesia with bupivacaine in a mouse model", Regional Anesthesia, 19(4): 264–269, 1994.

Hagen, et al., "Comparative clinical efficacy and safety of a novel controlled release oxycodone formulation and controlled–release hydromorphone in treatment of cancer pain", Cancer, 79(7): 1428–1437, 1997.

Hanks, G.W., "Cancer pain and the importance of its control", Anti–Cancer Drugs, 6(3): 14–17, 1995.

Hanks, et al., "Opioid responsiveness", Acta Anaesthesiologica Scandinavica, 41: 154–158, 1997.

Hargreaves, et al., "A new and sensitive method for measuring thermal nociception in cutaneous intrathecal hyperalgesia", Pain, 32: 77–88, 1988.

Hays, et al., "Comperative clinical efficacy and safety of immediate relese and controlled release hydromorphone for chronic severe cancer pain". Cancer, 74(6): 1808–1816, 1994.

Lafont, et al., "Use of liposome–associated bupivacaine in a cancer pain syndrome", Anaesthesia, 51(5):578–579, 1996.

Lawfor, et al., "Dose radio between morphine and hydromorphane in patients with cancer pain: a retrospective study", Pain, 72(1–2): 79–85, 1997.

Le Corre, et al., "In vitro controlled release kinetics of local anesthetics from poly(D,L–lactide) and poly(lactide–co–glycolide) microspheres", Journal of Microencapsulation, 14(2): 243–255, 1997.

Lee–Son, et al., "Stereoselective Inhibition of Neuronal Sodium Channels by Local Anesthetics", Anesthesiology, 77(2): 324–335, 1992.

Lesser, et al., "In vitro and in vivo studies of subcutaneous hydromorphone implants designed for the treatment of cancer pain", Pain, 65(2–3): 265–272, 1996.

Malinovsky, et al., "Neurotoxicological assestment after intracisternal injection of liposomal bupivacaine in rabbits", Anesthesia and Analgesia, 85(6): 1331–1336, 1997.

Malinovsky, et al., "Motor and blood pressure effects of epidural sustained release bupivacaine from polymer microspheres: A dose–response study in rabbits", Anesthesia and Analgesia, 81(3): 519–524, 1995.

Masters, et al., "Sustained local anesthetic release from bioerodible polymer matrices: a potential for prolonged regional analgesia", Pharmaceutical Research, 10(10): 1527–1532, 1993.

Moulin, et al., "Comparison of continuous subcuateneous and intravenous hydromorphone infusions for management of cancer pain", The Lancet, 337: 465–468, 1991.

Parker, et al., "Epidural patient–controlled analgesia: influence of bupivacaine and hydromorphone basal infusion on pain control after cesarean delivery", Anesthesia and Analgesia, 75(5): 740–746, 1992.

Payne, R., "Factor influencing quality of life in cancer patients: the role of transdermal fentanyl in the management of pain", Seminars in Oncology, 25(3): 47–53,1998.

Renck, et al., "Slow release formulations of local anesthetics and opioids", Current in Anesthesiology, 9: 399–403, 1996.

Rhodes, et al., "Hydromorphone Polymer Implant", Journal of Substance Abuse Treatment, Journal of Substance Abuse Treatment, 14(6): 535–542, 1997.

Singh, et al., "Effects of ketorolac versus bupivacaine co–administration during patient–controlled hydromorphone epidural analgesia after thoracotomy procedures", Anesthesia and Analgesia, 84(3), 564–569, 1997.

Sjoberg, et al., "Nueropathologic findings after long–term intrathecal infusion of morphine and bupivacaine for pain treatment in cancer patients", Anesthesiology, 76(2): 173–186, 1992.

Suri, et al., "Pharmacokinetic–pharmacodynamic relationships for analgesics", International Journal of Clinical Pharmacology and Therapeutics, 35(8):307–323, 1997.

Vainio, et al., "Opioid treatment for radiating cancer pain: oral administration vs. epidural techniques", Acta Anesthesiologica Scandinavica, 32: 179–185, 1988.

van Dongan, et al., "Neurological impairment during long–term intrathecal infusion of bupivacaine in cancer patients: a sign of spinal cord compression", Pain, 69(1–2): 205–209, 1997.

Vercauteren, et al., "Addition of bupivacaine to sulfentanil in patient controlled epidural analgesia after lower limb surgery in young adults", Regional Anesthesia and Pain Medicine, 23(2): 182–188, 1998.

Vigano, et al., "Individualized use of methadone and opioid rotation in the comprehensive management of cancer pain associated with poor prognostic indicators", Pain, 67(1): 115–119, 1996.

Wu, et al., "The efficacy of intrathecal coadministration of morphine and bupivacaine for labor analgesia", Acta Anaesthesiologica Scandinavica, 35: 209–216, 1997.

Okuda, et al., "Prolonged antinociceptive effect of poly (DL–lactic acid)–fentanyl composites after their intrathecal injection in rats" (in Japanese), Masui—Japanese Journal of Anesthesiology, 48(2): 141–145, 1999, with Abstract in English.

* cited by examiner in the experiment with double dose (t-test):
* $p < 0.05$ control group vs HM, BP and HM + BP group
x $p < 0.05$ HM + BP group vs HM group and BP group
^ $p < 0.05$ HM group vs BP group

DRUG DELIVERY COMPOSITION

This application claims priority to provisional application U.S. Ser. No. 60/310,434, filed on Aug. 6, 2001 the entire contents of which is hereby incorporated by reference.

FIELD OF THE INVENTION

The invention relates to the alleviation of pain.

BACKGROUND OF THE INVENTION

Pain is one of the most feared symptoms for patients with cancer and other serious diseases. It is defined by the International Association for the Study of Pain as "an unpleasant sensory and emotional experience associated with actual or potential tissue damage, or described in terms of such damage" (Suri et al., Pharmacokinetic-Pharmacodynamic Relationships for Analgesics, International Journal of Clinical Pharmacology and Therapeutics, 35(8), 307–323, 1997). Pain control is important for patients suffering from cancer, as well as post-surgical patients.

SUMMARY OF THE INVENTION

The invention provides drug delivery compositions and methods for treating pain, e.g., neuropathic pain. A drug delivery composition contains a biodegradable polymer and at least two drugs (e.g., an analgesic and an anesthetic). The first drug is an anesthetic and a second drug is an analgesic. An analgesic composition is an agent that leads to loss of pain following administration to a subject without loss of conciousness of the subject. An opioid analgesic composition is a naturally-occurring purified agent or synthetic agent that binds specifically to a mammalian opioid receptor, or has a chemical structure related to that of a naturally-occurring opioid. An opioid composition includes agents, which have the same or similar pharmacological effects as morphine, e.g., pain relief.

An anesthetic composition is an agent which leads to loss of sensation. Preferably, the composition is a local anesthetic, e.g., loss of sensation at a specific site is achieved following contact of the agent with a bodily tissue at the site of an injured tissue such as a wound, surgical incision, infection, or cancer.

The device contains a drug and a polymer. For example, the drug component of the composition is in the range of 0.1–70% w/w relative to the polymer component. Preferably, the drug component is 20%, 25%, 45%, 50%, or 60% by weight of the device. In addition to drug and polymer, the device optionally contains other pharmaceutically-acceptable agents, e.g., a buffering agent such as hydroxyapatite, a diluent, or a hygroscopic compound. A hygroscopic compound is one that readily takes on water. A device comprising a hygroscopic compound absorbs water following implantation into a bodily tissue. As a result, the rate of drug release from the polymer into surrounding tissue is increased.

The first drug, an anesthetic, is preferably bupivacaine. Alternatively, the anesthetic is 2-chloroprocaine, lidocaine, mepivacaine, ropivacaine, mepivacaine, benzocaine, tetracaine, dibucaine, cocaine, or prilocaine. The second drug is an opioid or opioid agonist. For example, the opioid is morphine or a morphine analog. Preferably, the opioid is hydromorphone. The opioid agonist is preferably biphalin.

The polymer is preferably shaped to fit into or adjacent to a bodily tissue or body cavity. For example, a polymer is shaped to fit within the spinal canal. The diameter of the device is in the range of approximately 2 mm to 0.5 cm.

The device is administered topically (e.g., on or into dermal tissue such as skin), locally (e.g., implanted or injected directly around a nerve supplying a painful area in nerve root blocks), or regionally (e.g., over several $cm^2$ or contacting several different tissue types affected by a surgical procedure). The ratio of said first drug and said second drug is 50:50, and the ratio is varied to accommodate the clinical needs of the patient. The device includes a pain-relieving composition in an amount that is at least 0.1% w/w of the device. The amount of drug present in the device ranges from 0.1–70% by weight, e.g., at least 25%, 50%, 65% w/w or more, to achieve a desired level of pain relief.

The device is extruded or molded in the shape of a body cavity. For example, the device is in the shape of a device that fits into a body lumen, e.g., a chest tube, endotracheal tube, surgical drain, or catheter. The device generally cylindrical in shape, e.g. the device is in the shape of a rod or a thread, e.g., for use as a surgical suture. For example, a method of therapy involves using a device in the shape of a thread, and the device is implanted by surgically suturing a wound. For most embodiments, the device does not contain microspheres.

The device contains a biodegradable polymer such as poly lactic-glycolic acid (PLGA), an alkanoid polymer, a poly-hydroxyacid polymer, or an anhydride polymer. The polymer is surface-erodible or bulk-erodible. For example, the device contains a copolymer of lactic acid and glycolic acid at a ratio of 75:25 (PLGA-75:25) or a copolymer of lactic acid and glycolic acid at a ratio of 50:50 (PLGA-50:50).

Also within the invention is a method of relieving pain in a subject, e.g., a human patient, by implanting into the subject a biodegradable polymer containing an analgesic and an anesthetic. The method achieves continuous pain relief, e.g., pain is alleviated for a prolonged period of time during which drug is released from the polymer. Pain-relief achieved by the multiple drug composition is synergistic, i.e., the clinical benefit to the subject is greater than the sum of the pain relief achieved by administering each drug alone. The methods and devices are also suitable for veterinary use, e.g., for treatment of pets such as dogs and cats, as well as livestock and other animals.

Administration is carried out by implanting or placing the device in a body cavity or adjacent to a bodily tissue, e.g., an injured or diseased tissue. For example, the device is placed parallel to a nerve such as a sciatic nerve. In another example, the device is implanted intrathecally. Intrathecal administration refers to administration of drug into a fluid or space surrounding the spinal cord or brain. For example, intrathecal administration involves release of drug into cerebrospinal fluid.

The rate of drug release is affected by the molecular weight of the polymer (the erosion rate), the amount of drug and the ratio of it to the carrier polymer, and the form of drug, which in turn, affects its solubility in the medium and in the polymer. The drug compositions is in the form of a salt. Drugs are released at a rate of approximately 1–10 mg/day, e.g., pain relieving compositions are released at a rate of 3.5 mg/day for several days, weeks, and up to a month or more.

The devices and methods described herein offer numerous advantages over standard approaches to relieving pain. For example, the device and method of treatment allow a lower amount of drug to be administered to the patient to achieve the same or similar degree of pain relief (compared to standard methods of administration). Thus, sustained, local release of drug using the polymers and drug formulations described herein is associated with decreased drug toxicity. Therefore, the risk of developing of drug tolerance (associated with continued systemic administration of drugs) is decreased with local polymer-mediated drug administration. Other adverse side effects of systemic opioid drug delivery, e.g., difficulty in concentrating, anxiety, blurred vision, impaired night vision, suppression of cough reflex, nausea, vomiting, constipation, loss of appetite, decreased gastric motility, sweating, and reduced libido, are also reduced compared to standard systemic drug delivery regimens.

Simultaneous administration of local anesthetics and opioids is an effective pain management approach. Presently, however, the modality necessary to administer this combination is via pumps or injections. Pump or injection delivery necessitates the presence of experts (i.e. medical professionals) during the initial application stage as well as during the continuation phase even when a patient-controlled approach is used, and these modes of administration require the patient to be hospitalized. The compositions and methods described herein allow delivery of drugs using an implantable system that reduces patient immobilization and the level of expert care required, e.g., hospitalization, compared to convention delivery systems. Simultaneous delivery of local anesthetics and opioids (and optionally other therapeutic agents) is achieved using an implantable controlled release systems.

Other features and advantages of the invention will be apparent from the following description of the preferred embodiments thereof, and from the claims. All patents and publications cited in this specification are incorporated herein by reference.

DETAILED DESCRIPTION OF THE INVENTION

Figure 1:
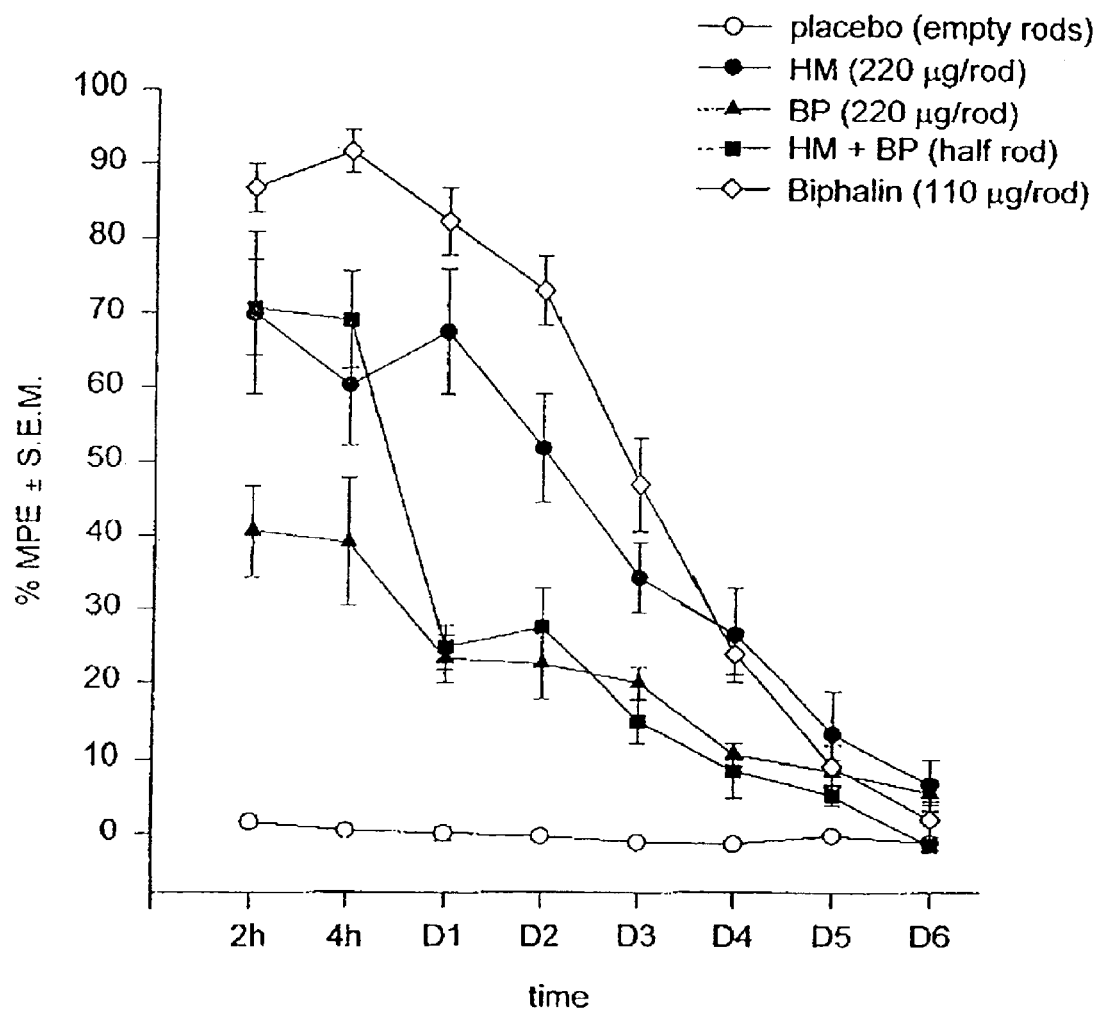
FIG. 1 is a line graph showing levels of pain after intrathecal implantation of PLGA rods with hydrophone (HM), bupivacaine (BP), HM+BP, or with biphalin measured by tail-flick test. The graph shows % MPE+/−standard error (S.E.M).

Pain management is achieved by simultaneous controlled release of both an analgesic agent and an anesthetic agent. A polymer is fabricated to contain multiple agents. Analgesic and/or anesthetic agents are released from the polymer at the site of greatest physiological relevance, e.g., in direct contact with or near a source of pain. The data described herein indicates that fabrication of a multi-drug polymer shaped so as to fit into or adjacent to an organ, body lumen or cavity, e.g., within the spinal canal, effectively alleviates pain in an art-recognized animal model for pain. The polymer is also shaped to fit into or adjacent to a wound or surgical incision, e.g., in the form of a surgical suture. Spinal analgesia is formulated in a drug polymer suited to fit into or adjacent to the spinal canal, e.g., in the form of a rod. Polymers that release analgesic and/or anesthetic drugs are also fabricated in the shape of a chest tube or surgical drain or other device or body cavity.

Dual drug delivery (or multiple drug delivery, e.g, three of more drugs) is accomplished by simultaneous controlled delivery of an analgesic, such as morphine or a morphine analog, in combination with an anesthetic. Although patients with intractable cancer pain had been studied previously during long term infusion of morphine and Bupivacaine (BP), this combination of drugs was generally administered as a last resort for the treatment of severe pain despite the absence of toxicity of this mixture to the meninges, nerve roots or spinal cord itself. Sjoberg et al. reinvestigated such problems with this combination (Neuropathological Findings after Long-term Intrathecal Infusion of Morphine and Bupivacaine for Pain Treatment in Cancer Patients, Anesthesiology, 76, 173–186, 1992). Infusions of a mixture of morphine and bupivacaine were carried out via a subcutaneously tunnelled Portex nylon catheter.

Cooper et al. (Patient Controlled Extradural Analgesia to Compare Bupivacaine, Fentanyl and Bupivacaine Fentanyl in the Treatment of Postoperative Pain, British J. of Anaesthesia, 70, 503–507, 1993) demonstrated that combining extradural BP and fentanyl decreased analgesic requirements of each individual agent.

Similarly both ketorolac and BP supplementation of HM patient-controlled epidural analgesia (PCEA) reduced the severities of pain on coughing and on movement compared with HM PCEA alone (Singh et al., Effects of ketorolac versus bupivacaine co-administration during patient-controlled Hydromorphone Epidural Analgesia after Thorocotomy Procedures, Anesth. Analg. 84(3), 564–569, 1997).

Vercauteren et al. showed that patients who received postoperative analgesia via PCEA with sulfetanyl alone or with 0.06% or 0.12% BP and patients receiving BP had better pain relief than those receiving only the opioid (Addition of bupivacaine to sulfetanil in patient controlled epidural analgesia after lower limb surgery in young adults: effect on analgesia and micturition., Reg. Anesth. Pain Med., 23(2), 182–188, 1998).

Morphine and BP used concomitantly intrathecal (i.t.) on 55 patients revealed that a single injection of intrathecal (i.t.) morphine and BP provided rapid onset and effective analgesia with manageable side effects and without major complications (Wu et al., The Efficacy of Intrathecal Coadministration of Morphine and Bupivacaine for Labor Analgesia, Acta Anaesthesiol. Sin. 35(4), 209–216, 1997).

Infusion is still a restricting mode of application, and the continuous provision of drugs without continuous connection to catheters remains a priority in pain relief treatment. Sustained release systems provide a promising treatment alternative by increasing patient mobility during drug administration. Codeine Contin in sustained release (150 mg/12 h) form was found to be equianalgesic to much higher doses of acetaminophen+codeine (600 mg+60 mg/6 h) (The Dose Response Relationship of Controlled-release Codeine (Codeine Contin) in Chronic Cancer Pain, J. Pain Symptom Management, 9(6), 363–371, 1994). However, even in this sustained release application the administration frequency is quite short (12 h).

Nevertheless, Hays et al. prepared a controlled release form of Hydromorpone with 12 h activity to prolong half-life and improve patient compliance as in the case of MS and Codeine Contin. This form was highly effective in the treatment of chronic, severe cancer pain (Comperative Clinical Efficacy and Safetey of Immediate Release and Controlled release HM for Chronic Cancer Pain. Cancer, 74(6), 1808–1815, 1994).

Curley et al. discovered that polymeric carriers were able to provide longer term releases. A typical example of these is the use of PLGA mainly in the form of microspheres. For example, PLGA was used to carry a combination of drugs (but not both analgesics). PLGA 65:35 microspheres loaded with 75% w/w bupivacaine alone or with 0.05% w/w dexamethasone were injected into rats and produced sciatic nerve block for 10 h–5.5 days as shown with thermal sensory testing as well as motor testing (Prolonged Regional Nerve Blockade, Injectable Biodegradable Bupivacaine/Polyester Microspheres, Anesthesiology, 84(6),1401–1410, 1996). The presence of dexamethasone increased the block duration ca. 13-fold attesting to the possibility of increasing the duration of activity by the use of a combination of drugs, and the potential value of decreasing local inflammation.

In a study by Malinovsky et al., Bupivacaine loaded poly(d,l-lactic acid) microspheres were introduced to rabbits via a chronically implanted epidural catheter (Neurotoxicological Assestment after intracisternal injection of liposomal bupivacaine in rabbits, Anesthesia and Analgesia, 85, 1331–1336, 1995). Significant delay in reaching maximum effects and prolongation of motor block (244%) were observed.

Another form of administering pain relief drugs employs the implantation of microspheres in the patient's body. However, microspheres, due to their large surface area and small size, tend to release rapidly and are hard to localize. Grossman and colleagues have developed a subcutaneous implant for controlled release of Hydromorpone (Lesser et al., In Vitro and In Vivo Studies of Subcutaneous HM Implants Designed for the Treatment of Cancer Pain, Pain, 65(2–3), 265–272, 1996; Grossman et al., U.S. Pat. No. 5,633,000; Rhodes et al., Polymer Implant, J Substance Abuse Treatment, 14(6), 535–542, 1997). This non-abusable, non-inflammatory, biocompatible and non-biodegradable implant delivered Hydromorpone with near zero order kinetics, e.g., at a constant rate.

Another Hydromorpone release system with hydrogel passages for drug delivery was designed for management of pain by Merrill et al., and disclosed in U.S. Pat. No. 5,529,787. In this system, the polymers carboxymethyl cellulose (CMC) and polyvinyl pyrrolidone were used to make the core and the implant had a polyethylene oxide coat with CMC gates to permit drug diffusion.

A transdermal fentanyl patch for the treatment of chronic cancer-related pain is available to deliver dosages of 25–100 g/h for 72 h (Payne, Factors Influencing Quality of Life in Cancer Patients: The Role of Transdermal Fentanyl in the Management of Pain, Semin Oncol. 25(3, Suppl. 7), 47–53, 1998). Unlike i.v. administration, where the plasma peak levels are reached in minutes with a plasma elimination half-life of 2–3 h, after the transdermal patch application peak levels are reached after 14 h and the half life exceeds 24 h. When compared with oral morphine, fewer gastrointestinal disturbances, better alertness and improved sleep quality were observed.

The advantages of simultaneous local anesthetic-opioid over previously-described methods include:

1. Reduction of sensorimotor block caused by high local anesthetic concentration.

2. Economical, especially when the anesthetic and opioid act synergistically.

3. Decreased the risk of tolerance development to opioids.

4. More effective pain management (local anesthetic during surgery and opioid for post-operative period) by using dual drug to manage different periods.

5. Capability to provide both rapid and prolonged pain management.

6. Reduction of side effects like toxicity, hypotension, sedation, nausea, vomitting, constipation.

Accordingly, an important goal of analgesic therapy is to achieve continuous relief from chronic pain. However, the currently available local anesthetics and opioid analgesics have a relatively limited duration of activity. Prolongation of their action would significantly benefit patients suffering from chronic pain. Recently, local anesthetics normally used for anesthesia in surgery have been supplemented with small doses of opioids to provide more efficient analgesia. The prolongation of pain relief is thus a major goal of present pain treatment regimens.

Approximately one-fifth of cancer patients are reported to receive inadequate pain relief (Ahmedzai, Current strategies for Pain Control, Annals of Oncology 8 (Suppl.3), 21–24, 1997). Pain control is also important for post-surgical patients. In each of the above contexts, use of analgesic drugs is the generally followed course of treatment for pain relief. An important goal of analgesic therapy is to achieve continuous relief from chronic pain. Currently available local anesthetics and opioid analgesics have a relatively limited duration of activity (due primarily to their short plasma half-lives) and some may cause severe toxicity due to their low LD50 values. Prolongation of the action of the drugs would significantly benefit the patients by lessening the amount of drugs administered, reducing the amount of drugs administered and thus decreasing toxicity that results from the administration of large quantities of anesthetics and analgesics. In turn, this leads to a slowing of the rate of tolerance that generally develops from the continued administration of these drugs.

Among the class of opioid analgesics, morphine is the prototype and standard for comparison (Goodman & Gilman's "The Pharmacological Basis of Therapeutics", eds: Goodman, L. S., Limbird, L. E., Milinoff, P. B., Gilman. A., Hardman, J. G., 9th ed., McGraw Hill, 1996). However, due to high solubilities and rapid excretion rates, morphine (or its derivatives) need to be taken frequently, such as every 4–6 h, with recurring pain at the beginning and the end of each period. Hydromorphone is an oxidation product of morphine, and like morphine, it has a short half-life, and is 4–8 times more potent than morphine. Hydromorphone is used as an alternative to morphine for administration via the oral and parenteral route in patients who require high doses or who have adverse reactions, such as histamine release, to morphine alone (WHO, Geneva, Cancer Pain Relief With a Guide to Opioid Availibility, 2nd ed., 1996, Lawlor et al., Dose Ratio Between Morphine and HM in Patients with Cancer Pain: A Retrospective Study, Pain, 72(1–2), 79–85, 1997).

Bupivacaine, on the other hand, is a local anesthetic used for spinal and epidural analgesia, and has been demonstrated to provide excellent anesthesia with minimal impairment of motor function even at very low concentrations. Bupivacaine primarily works by blocking motor axons (Dietz and Jaffe, Bupivacaine Preferentially Blocks Ventral Root Axons in Rats, Anesthesiology, 86, 172–180, 1997). However, the risk of hypotension must be considered especially after its epidural application (McGuire et al., Cancer Pain Management, Jones and Bartlett Publishers, Second Ed., 1995).

Presently, as a result of compelling preclinical data, local anesthetics used to provide single dose spinal anesthesia for surgery are supplemented with small doses of intrathecal opioid (eg. meperidine, fentanyl, morphine) to secure postoperative analgesia (Carr and Cousins, Spinal Route of Analgesia. Opioids and Future Options. in: Cousins M J, Bridenbaugh P O, eds., Neural blockade in clinical anesthesia and management of pain. Phildelphia: Lippincott-Raven: 915–83,1998). After major surgery or trauma, epidural infusion of a combination of local anesthetic plus opioid is now the worldwide standard by which other methods of acute pain management are judged. The value of such combinations for movement-related pain has led to their adoption outside the acute care setting, such as for example, for the chronic management of cancer-related and non-malignant pain. Spinal application of non-opioid plus opioid analgesics may have not only a dose-sparing effect, but also a tolerance impeding effect. Keeping the concentration of the local anesthetic low (eg. BP below 0.1%) minimizes the incidence of sensorimotor block during both acute and chronic infusion.

It was possible to provide pain relief for prolonged periods with a single application of two drugs. This is a significant improvement over current application methods. The more effective pain relief with use of two different drugs simultaneously (the dual drug approach) confirmed the results of the recent applications via intrathecal and epidural routes. It is thus shown that dual drug controlled release systems have a potential for prolonged pain management.

Currently available local anesthetics and opioid analgesics have a relatively limited duration of activity (due to their short plasma half-lives) and some may cause severe toxicity due to their low LD50 values. Prolongation of action would significantly benefit the patients, help use less drug, lower toxicity, and development of tolerance might also be more gradual. The recent trend in pain management involved coupling of two drugs, one a local anesthetic and the other an opioid for more effective pain management to achieve rapid and long-term relief with the use of less analgesics.

The applications along this direction involved continuous intravenous (i.v.) or intrathecal (i.t.) administrations to prolong the duration and is an approach that immobilizes the patients, leads to pain, requires patient compliance and continual care by professionals. In a very succesful example of such an application, Dahm et al. used long term, continuous intrathecal (i.t.) opioid (buprenorphine 0.015 mg/mL, 0.114 mg/day) and bupivacaine (bupivacaine 4.75 mg/mL, 37 mg/day) analgesia in a case not amendable to corrective surgery due to the absence of any reliable method for long-term (more than 6 years) treatment of severe pain following complications of hip arthroplasty. (Dahm et al., Six years of Continuous Infusion of Opioid and Bupivacaine in the Treatment of Refractory Pain Due to Intrapelvic Extrusion of Bone Cement After Total Hip Arthroplasty, Reg Anesth Pain Med, 23(3), 315–319, 1998). This dual i.t. treatment provided the patient with 85–100% relief and mobility to carry out everyday activities.

Continuous subcutaneous (s.c.). infusion using portable infusion pumps has been demonstrated to carry all the advantages of continuous i.v. infusion with the added benefits of greater mobility, management on an outpatient basis, and avoidance of the need for i.v. access (Moulin et al., Comparison of Continuous Subcuateneous and Intravenous Hydromorphone Infusions for Management of Cancer Pain, The Lancet 137,465–468,1991).

Pain Relief Compositions

Compositions useful to alleviate pain include analgesic agents, e.g., opioids, and anesthetic agents, e.g., amide or ester anesthetic agent.

An opioid agonist is a natural or synthetic substance which binds specifically to an oid receptor. Opioid analgesics reduce the perception of pain without a loss of consciousness. The 4,5-epoxy-methylmorphinan opioid alkaloids morphine, codeine and thebaine are natural-products on which analgesic analogs are modeled. Morphine itself has a variety of effects, such as increased tolerance to pain, somnolence, euphoria, antitussive effect, respiratory depression, constipation and emesis. Morphine has a high addiction liability. Derivatives of morphine have been sought that retain the analgesic activity of the parent, but that have improved oral bioavailability and a reduction in addiction liability and other deleterious side effects.

Opioid analogs, have been developed with a progressive simplification of chemical structure from the epoxymorphinans (nalorphine, nalbuphine) through the morphinans such as levorphanol, and the benzomorphans such as pentazocine, to the phenyl-piperidines including pethidine and the 4-anilino-piperidines as exemplified by fentanyl. The ultimate simplification of the morphine structure was in the methadone class, with methadone itself and d-propoxyphene. Although thebaine is virtually inactive, the compound itself was an important chemical precursor in the synthesis of 14-hydroxy derivatives of morphine, most particularly the antagonists naloxone and naltrexone. Also derived from thebaine were the oripavine derivatives, and here the trend of chemical "simplification" was reversed with the introduction of an additional six-membered ring that appeared to enhance biological potency. For example, etorphine is about one thousand times more potent than morphine as an analgesic.

The structure of morphine is shown below as Formula I. The rings are lettered A (aromatic), B (cyclohexane), C (cyclohexene), D (piperidine) and E (tetrahydrofuran). All of the derivatives of morphine which possess this basic ring structure have a high addiction liability which is proportional to their analgesic activity.

Formula I

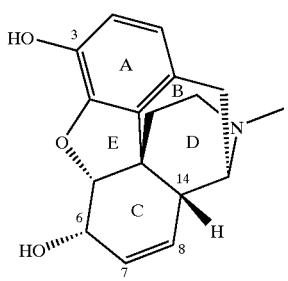

Some morphine derivatives result from modifications at the 3- and 6-hydroxyl groups. Conversion of the 3-OH to a 3-OCH3, yields codeine. Groups larger than a methoxy reduce activity dramatically. Conversion of the 6-OH to a 6-OCH3, yields heterocodeine. Oxidation of the 6-OH to a ketone (morphinone) reduces activity when the 7,8-double bond is present. However when the 7,8-double bond is saturated, a 6-keto will increase activity. Removal of the 6-OH yields 6-desoxymorphine. Acetylation of both the 3- and 6-OH produces 3,6-diacetylmorphine, also known as heroin. Heroin is 2–3 times more potent than morphine. Most of this increase is due to increased lipid solubility, which leads to enhanced and rapid CNS penetration. The 6 position can be substituted with a methylene substituent to produce 6-methylene-dihydromorphine.

Morphine modifications may also occur at the 7,8-double bond. For example, reduction of the 7,8-double bond results in a slight increase in activity, as in dihydromorphine and dihydrocodeine. As mentioned above, saturation of the 7,8-double bond has the greatest effect when combined with modifications at the 6-position (as in dihydromorphinone).

Other modifications occur at the nitrogen substituent. Methyl is the optimal substituent for agonist activity, and ethyl is passable. If the nitrogen substituent is a hydrogen, analgesic effect is reduced and addiction liability is lowered. Addition of a phenethyl substituent in place of methyl results in a 14-fold increase in activity over morphine. Quaternary ammonium derivatives such as N,N-dimethylmorphine have no analgesic activity, but do have significant curare-like activity. If the nitrogen substituent is a bulky alkyl group such as propyl, isobutyl, or especially allyl and cyclopropylmethyl, the compound becomes a narcotic antagonist.

Nuclear (ring) substitutions also result in morphine analogs, as does opening up the ether linkage (E ring) to form the catechol-type ring system.

Addition of a 14-beta-OH results in a dramatic increase in activity in the dihydromorphinone series of morphine analogs.

Representative morphine analogs include codeine, heterocodeine, morphinone, dihydromorphine, dihydrocodeine, dihydromorphinone, dihydrocodeinone, 6-desoxymorphine, heroin, oxymorphone, oxycodone, 6-methylene-dihydromorphine, hydrocodone, hydromorphone, metopon, apomorphine, normorphine, N-(2-phenylethyl)-normorphine, and oripavine derivatives such as etorphine and buprenorphine.

Certain structural features are found in most opioid analgesic analogs, and are collectively referred to as the "Morphine Rule". There are, however, some exceptions to this rule. The common features include: a tertiary nitrogen with a small alkyl substituent; a quaternary carbon; a phenyl group or its isosteric equivalent directly attached to the quaternary carbon; a 2 carbon spacer between the quaternary carbon and the tertiary nitrogen.

One class of morphine derivatives, called morphinans, lack the tetrahydrofuran (E) ring found in morphine. These opioids typically also lack the 6-OH and the 7-8-double bond. The general structure can be represented by levorphanol, represented by Formula II:

Formula II

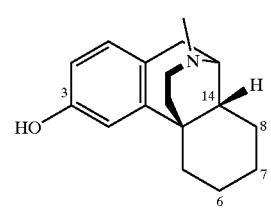

The structure/activity relationships of the morphinans are very similar to those of the morphines, for example, a 3-OH is optimal, and a 3-methoxy is less active; the nitrogen substituent produces the same activity as in the morphines; no other substituents may be added to the A ring; the C ring must be unsubstituted. Examples of morphinans include levorphanol (above), racemorphan, levallorphan, dextromethorphan, cyclorphan, and butorphanol.

Another class of morphine derivatives include benzomorphans, which lack the C and E rings found in the naturally occurring opioids. The general structure is represented by Formula III:

Formula III

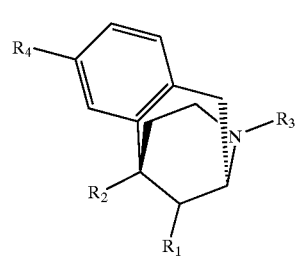

The structure/activity relationships of the follow the same pattern as the morphinans. The nitrogen substituent (R3) follows the same rules as the morphinans and morphines. R1 and R2 substituents must be present to supply vestiges of the C ring. These are usually methyl, or a similar lower alkyl. R2 must be alpha for the analog to have agonist activity. R1 can be alpha (cis), producing analogs with activity about equal to morphine, or beta (trans), producing agents 4–30 times as active as morphine. The beta agents will support narcotic addiction, while the alpha series will not. R4 must be OH or methoxy. Representative benzomorphan analogs include phenazocine, pentazocine and cyclazocine.

4-Phenylpiperidines are compounds which fall within the "Morphine Rule". The representative 4-phenylpiperidine is meperidine, as shown in Formula IV:

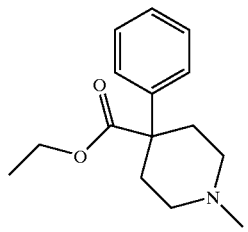

Formula IV

Some structure/activity relationships of 4-phenylpiperidines Include the following: both esters and reverse esters at the 4 position are active, as are the simple ketones. propyl is the optimal chain length (excluding the ester oxygen); the phenyl ring at the 4 position is necessary for activity, and must be able to assume the axial position; addition of a m-OH group will enhance activity; such analogs are called bemidones; if a reverse ester is combined with a 3-methyl, the analogs are known as prodines. The methyl group may cause enantiomeric recognition by the opioid receptor. The nitrogen substituent is a methyl in most cases. A phenethyl or its equivalent will increase activity. It is not possible to confer antagonist activity with a nitrogen substituent such as allyl. Representative 4-phenylpiperidines include meperidine (above) diphenoxylate, ketobemidone, anileridine, piminodine, fentanil, ethoheptazine, alphaprodine, betaprodine, 1-methyl-4-phenyl-1,2,5,6-tetrahydropyridine (MPTP), loperamide, sufentanil, alfentanil, remifentanil, and lofentanil.

Other opioid analgesics include open chain opioid analgesics. Open chain analogs which follow the morphine rule can have significant analgesic activity. The general structure of these compounds is represented by Formula V:

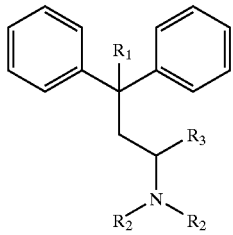

Formula V

The structure/activity relationships of open chain opioid analgesics is as follows: both phenyl groups must be present; the nitrogen substituent R2 can vary, but the nitrogen should be tertiary. a m-OH reduces activity; the (−)-isomers are most potent; R1 is usually propionyl; R3 is usually methyl, and the total aliphatic chain length is usually 7 carbons. Representative examples include methadone, isomethadone, Levo-alpha-acetylmethadol (LAAM), and propoxyphene.

The opioid receptor has three main binding areas. There is an anionic site (8 by 6.5 angstroms) that bonds to the charged nitrogen of morphine, a cavity which accommodates the piperidine ring, and a flat surface for binding the aromatic portion of the molecule. All active agonists and antagonists fit this receptor to some degree. There are four receptor subtypes, termed mu (the morphine receptor), sigma (the phencyclidine receptor), kappa (the ketocyclazocine receptor) and delta (the endorphin/enkephalin receptor).

Three well-defined or "classical" types of opioid receptor $\mu$, $\delta$ and $\kappa$ have been described. Genes encoding for these receptors have been cloned. More recently, cDNA encoding an "orphan" receptor was identified which has a high degree of homology to the "classical" opioid receptors; on structural grounds this receptor is an opioid receptor and has been named ORL1 (opioid receptor-like). All of the cloned opioid receptors possess the same general structure of an extracellular N-terminal region, seven transmembrane domains and intracellular C-terminal tail structure. There is pharmacological evidence for subtypes of each receptor and other types of novel, less well-characterized opioid receptors, $\epsilon$, $\lambda$, $\iota$, $\zeta$, have also been postulated.

Generally, opioid compounds have highest affinity for the $\mu$receptor, and produce the effects obtained with morphine. Depending on the level of affinity and efficacy, such compounds are used to provide analgesia in cases of mild, through moderate to severe pain, alone or with other pain-releving agents. The piperidines related to fentanyl include the most potent non-peptide $\mu$-agonists known, and are generally used peri-operatively, often for the induction and maintenance of anesthesia. The use of many of the benzomorphans (as had been found with the first of the "duallists" nalorphine) has been associated with dysphoric and psychotomimetic effects in man, a property originally thought to be attributable to affinity at the non-opioid $\sigma$-site.

Selective $\kappa$-agonists analgesics include 6,7-benzomorphans such as ketazocine and its derivatives. Arylacetamides appear unrelated structurally to any of the morphine derivatives, but are highly selective agonists of the $\kappa$-receptor. This class includes U-50,488, which has been used as a chemical lead for the design of related compounds with greater selectivity and potency. Two such compounds as centrally acting analgesics include Spiradoline (U-62, 066) and enadoline (CI-977). Analogs with limited brain penetration to produce a peripherally mediated analgesic effect in inflammatory conditions include asimadoline and EMD-61753.

The discovery of the enkephalins and of the $\delta$-receptor, led to the idea that the peptides themselves might be taken as "leads" for the synthesis of a new class of opioid agonist that lacked the addictive properties of morphine. Activation of the $\delta$-receptor is associated with antinociception in animals. Such compounds include a 6,7-indole analogue of naltrexone, naltrindole. $\delta$-agonists have a superior profile as analgesics.

An anesthetic is a substance that causes lack of feeling or awareness. For example, a general anesthetic is an agent that depresses the central nervous system reversibly, producing loss of consciousness, analgesia, and muscle relaxation, with minimal depression of a patient's vital functions. That is, a general anesthetic agent places the patient in a state of anesthesia in which his muscles are relaxed and he feels no pain. Regional anesthesia affects a limited part of the body, and it does not make the patient unconscious. Spinal and epidural anesthesia are examples of regional anesthesia. A local anesthetic causes loss of feeling in an even smaller part of the body. For example, a local anesthetic can be applied topically, to numb a defined area.

Local anesthetics in common use include agents of short, intermediate, and long duration. Local anesthetics vary in their chemical components, structure and activity relationships, and potency. A typical local anesthetic structure contains a hydrophilic domain (e.g., a tertiary amine but may be a secondary amine) and hydrophobic domain (aromatic moiety) separated by an intermediate ester or amide linkage. Some local anesthetics do not have an amide or ester linkage. A broad range of compounds contain these minimal structural features and act as local anesthetics. These anesthetics are classified according to the type of linkage they possess, and the nature of the linkage group determines an anesthetic's pharmacologic properties. For example, local anesthetics with an ester link are readily hydrolyzed by plasma esterases. Amide-linked local anesthetics are metabolized via hepatic endoplasmic reticulum. Other factors that influence their pharmacologic properties and toxicity are hydrophobicity, molecular size, pH, and route of exposure. Local anesthetics bind to specific receptors within the pores of neuronal cell membrane sodium channels, blocking ion movement. This prevents neurons from reaching action potential, thereby interrupting nerve impulses and reducing pain. The action of local anesthetics is restricted to the application site and reverses when the anesthetic diffuses from the site of action within the nerve. See, generally, Hardmen et al., Goodman and Gilman's, The Pharmacological Basis of Therapeutics, $9^{th}$ Ed. McGraw-Hill, Health Professions Division, 1996, 331–347; and Leeson et al., Anesthesiology, 1992. 77:324–335.

One example of a long lasting amide local anesthetic is bupivacaine, shown as Formula VI:

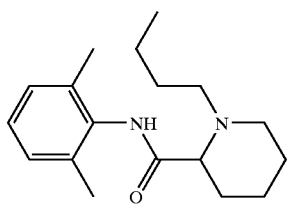

Formula VI

Some local anesthetics include 2-chloroprocaine (short-acting ester local anesthetic); lidocaine (amide local anesthetic of intermediate duration), mepivacaine (amide local anesthetic of intermediate duration), ropivacaine (long acting amide, related in chemical structure to bupivacaine and mepivacaine). Others include benzocaine, tetracaine, dibucaine, cocaine, and prilocaine.

Tissue Targetted Pain Relief

The methods described herein overcome many of the adverse side effects of systemic administration of pain-relieving drugs, because the drug is targetted to a source of pain. Since the drug is targetted and delivered regionally or locally, less drug is needed to alleviate the subject's pain.

Regional treatment refers to drug delivery that leads to a "region" of the body being anesthetized without making the person unconscious. Regional pain alleviation include administration of drugs spinally or epidurally. A drug or combination of drugs is administered, e.g., a drug-loaded polymer composition is implanted, into the spinal canal to cause a loss of sensation of the lower body. Spinal anesthesia is used for surgery on the legs or lower abdomen. Epidural anesthesia, which also leads to loss of sensation in the legs and lower abdomen, is carried out by administering a pain-relieving composition into a space outside the spinal canal, i.e., the epidural space. For example, a rod is placed into the epidural space and drug is released by diffusion and as a result of polymer degradation over time, e.g, over a period of several days, weeks, and up to a month or more. Regional techniques are also used to block specific areas such as one foot, one leg, one arm, or one side of the neck. In these cases, a smaller group of nerves is blocked by implanting pain-relieving compositions adjacent to or near a specific area of pain.

Polymers

Polymers to be used in the device are biodegradable, i.e., the polymer degrades in vivo over a period of less than a year. For example, at least 50% of the polymer degrades within six months or less. The polymer degrades significantly within a month, with at least 50% of the polymer degrading into non-toxic residues which are removed by the body, and 100% of the drug being released within a two week period. Polymers degrade by hydrolysis, by surface erosion, or by bulk erosion. Suitable polymer compositions include polyanhydrides and co-polymers of lactic acid and glycolic acid. The weight ratio of lactic acid to glycolic acid is 4:1 (i.e., 80% or less lactic acid to 20% or more glycolic acid by weight) or more. Polyorthoesters containing a catalyst or degradation enhancing compound are also used. For example, the polyorthoesther contains at least 1% by weight anhydride catalyst such as maleic anhydride. Other useful polymers are known in the art, e.g, as described in U.S. Pat. No. 5,618,563.

Polymer compositions are loaded with therapeutic agents (e.g., pain-relieving medicaments) according to known methods, e.g., methods described in U.S. Pat. Nos. 5,456,917 and 5,718,921. The manufacturing process is carried out at a temperature at or below 37 degrees Centigrade. Drugs are preferably loaded into polymer compositions by dry processing rather than by wet processing. For example, the drug composition is dissolved in a solvent such as acetic acid and freeze-dried prior to combining the drug composition with the polymer composition. A polymer in the form of an extrudate, fibrous precipitate, or a foam is ground and blended with the freeze-dried drug composition. Both polymer and the pain-relieving drug composition may be mixed as dry powders. The mixture is then extruded into desired shapes and forms under pressure. For example, the extruding step is carried out under 20,000 tons of pressure. Alternatively, the extrusion is carried out at 40,000 tons of pressure and up to 100,000 tons of pressure.

Rods are manufactured in a variety of sizes and shapes. Cylinders or rods range in diameter from 2 mm to approximately 0.5 cm. For example, rods with a diameter of 5, 6, 7, 8, 9, or 10 mm are suitable for epidural or spinal implantation. Smaller diameter devices, e.g., those with a diameter of about 2–4 mm are useful as a thread or surgical suture. Larger diameter rods or hollow tubes are used as stents, drainage tubes, and other devices that fit into body cavities.

The resulting drug-loaded polymer releases drug at a rate of 0.1–25 mg/day. For example, drug is released at a rate of 3.5 mg/day. The degradation rate of the device is such that full release of the drug is achieved in a period of approximately 1 week to 1 month. In some cases, release of drug over a period of 2–3 months is preferred.

Rat Model for Pain

Rats were subjected to pain by constriction of their sciatic nerve of the right leg and drug release rods containing HM, or BP, or no drug were implanted to provide relief as measured by changes in their paw withdrawal thresholds. HPLC with electrochemical detectors and UV spectrophotometry were used for the determination of the drug content of the rods. Scanning electron microscopy was employed for obtaining morphological information.

In vitro release from the rods was achieved for a duration of at least 10 days. In vivo rods containing 5 mg of either drug could not provide relief for rats except when the two were used simultaneously. Upon increasing the dose two fold, by implanting two rods instead one, the effects of rods containing only one type of drug became detectable and the dual drug application was the most efficient. In the single dose case, no drug was detectable in the rat plasma. Rods retrieved after termination of in vivo test showed significant release with HM but suppressed release with BP.

Scanning Electron Microscopy

Scanning electron micrographs of the drug-loaded rods (before and after in vivo tesing) were obtained after coating with gold or carbon (depending on the frailty of the sample).

EXAMPLE 1

In Vivo Testing, Sciatic Blockade

Experiments were performed on adult (205–275 g) male Sprague-Dawley rats housed in groups of three per cage in a controlled 12 hour light/12 hour dark environment. Animals had free access to food and water at all times. The sciatic nerve ligation was done according to standard methods. All rats received the surgical intervention, the right side was the treated side (ligation and rods placement), the left side remained untouched. At the time of surgery, rats were anesthetized with 3% isoflurane delivered via a nose cone. The right sciatic nerve was exposed at the level of the mid-thigh by blunt dissection through the biceps femoris. Approximately 10 mm of the nerve was freed of adhering tissue, and two 3-0 silk ligatures were tied loosely around the nerve with 1–2 mm between ligatures. The nerve was barely constricted when viewed under the microscope. Rods were placed parallel to the nerve and secured on place with loose ligature. The number of rods placed depended on the total dose of drugs chosen: two rods (in the first series of study) and four rods (in the second series of study). After the placement of the rods the incision was closed with 3-0 silk suture, and rats were allowed to recover from the general anesthesia. All animals postoperatively showed a mild eversion of the affected paw. Rats showed also a normal grooming behavior, and normal weight gain (weight gain was monitored every other day for the duration of experiment). The rats were divided into four groups: control (received two polymer rods without drugs), and three treated groups: one received one rod with 2 mg of hydromorphone (HM) and one control rod, second—one rod with 2 mg of bupivacaine (BP) and one control rod, and third—one rod with 2 mg of HM and one rod 2 mg of with BP. In the second part of experiment the number of rods were doubled. All groups consisted of 6 rats.

The pain behavior assessment was performed according to standard methods. Unrestrained rats were placed in a clear plastic chamber (12.5×17×29 cm) with a glass floor and allowed to acclimate for approximately 15 minutes. Withdrawal responses to thermal stimulation were determined using 70 V source of visible light (emitted through a circular aperture of 4.5 mm diameter) which was placed 12 mm beneath a hind paw. Removal of the paw caused termination of the test and determined the pain threshold. The cut off time was established on 16 seconds to avoid paw damages. The testing was repeated 5 times for right and left hind paws with approximately 3–5 minutes between measurements. Rats were tested before the surgery (baseline threshold), and 1 hour and 2 hours after the rods placement. Day of surgery was considered the day 1 of experiment. Further testing was performed on day 2 and every other day for 12 days. Analgesia was expressed as a paw withdrawal threshold (sec), and as the area under the curve (AUC) of withdrawal threshold versus time. The data obtained during the paw withdrawal test were also presented as a difference score (DS) calculated from subtracting the treated (right) side from the control (left) side, and the area under the curve (AUC) of the difference score (DS) versus time. The negative DS indicates hyperalgesia. Data were analyzed by means of one way ANOVA and t-test to compare differences between groups. P value of <0.05 was considered statistically significant.

Blood samples were collected from each animal by nicking the tail before the rods placement and 3 hours later and then on the day 2, and on alternate days for 12 days. Blood samples (approximately 300–500 ml) were always drawn after the behavioral testing. After drawing, blood was left at room temperature to clot for 1 hour, and then was centrifuged at 9000 rpm for 6 minutes. The serum was collected and frozen at −80° C. until measurement of drug concentration by HPLC. On the day 12, rats were euthanized with carbon dioxide, and the rods were removed and store at 4° C. until further testing for remaining contents of active agents.

Assessment of Nerve Blockade

The effectiveness of nerve blockade by the local anesthetic and the systemic opioid a modified hot plate test was applied. Hind paws were subjected to a beam of light and the time that the animal left its paw on the bottom of the plexiglass cage was recorded as paw withdrawal threshold. This test was carried out first with the right and then with the left paw. The test was repeated É times with each of the 6 rats for each time point.

Figure 2A:
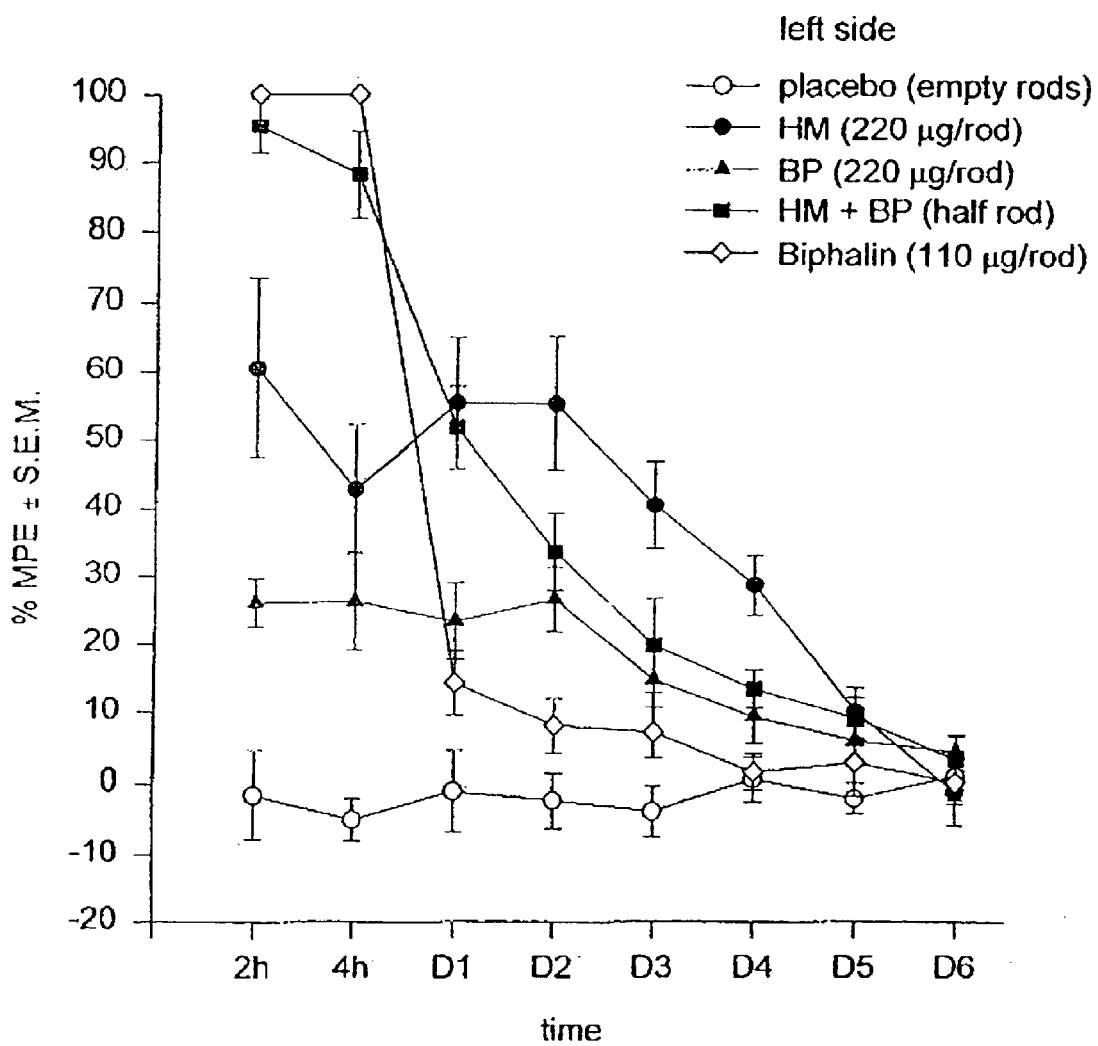
FIG. 2A is a line graph showing levels of pain after intrathecal implantation of PLGA rods with hydrophone (HM), bupivacaine (BP), HM+BP, or with biphalin measured by paw withdrawal test. (left side). The graph shows % MPE+/−S.E.M.
Figure 2B:
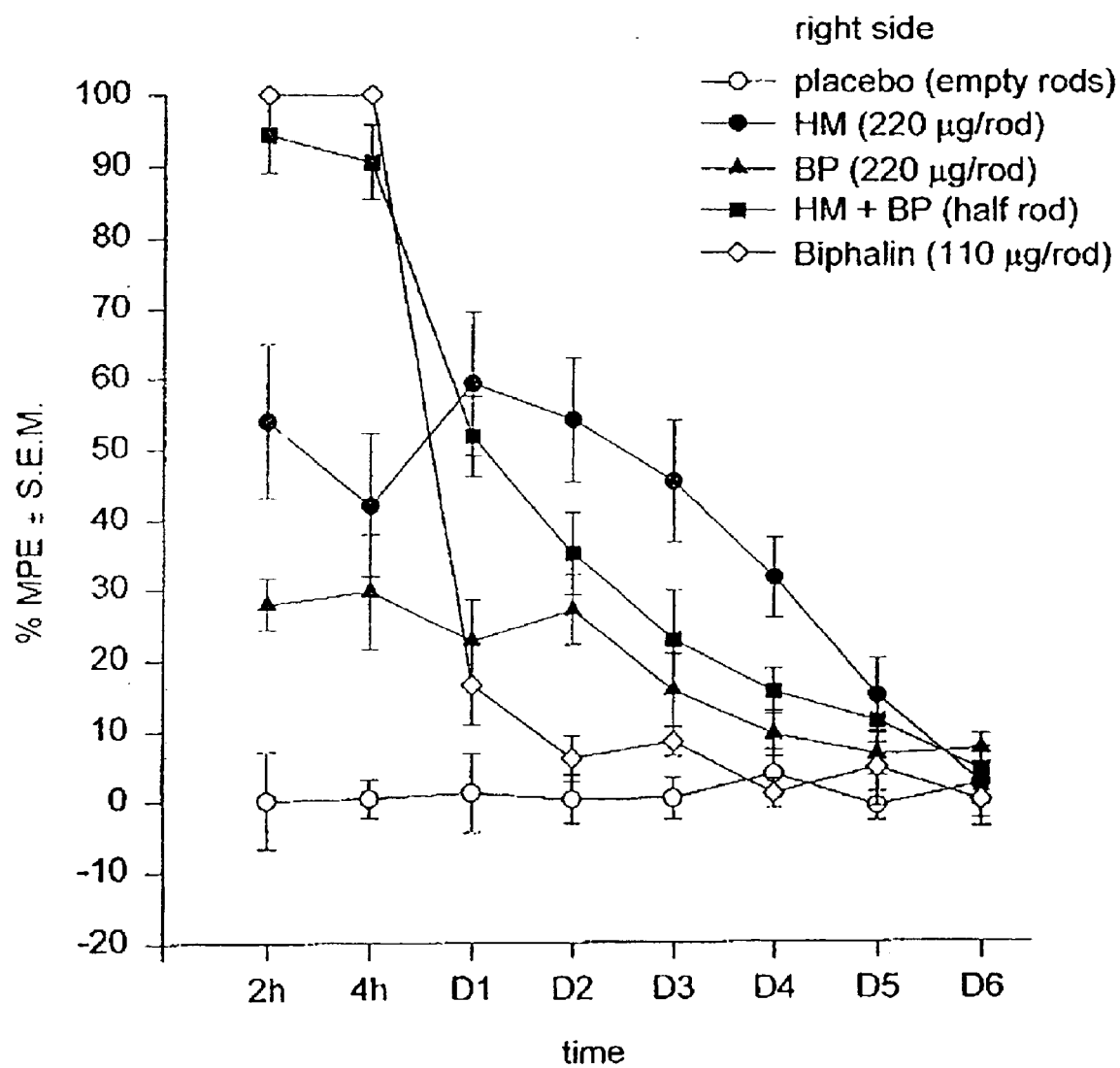
FIG. 2B is a line graph showing levels of pain after intrathecal implantation of PLGA rods with hydrophone (HM), bupivacaine (BP), HM+BP, or with biphalin measured by paw withdrawal test (right side). The graph show % MPE+/−S.E.M.

FIG. 1 shows levels of pain after intrathecal implantation of PLGA rods with hydrophone (HM), bupivacaine (BP), HM+BP, or with biphalin measured by tail-flick test. Table 2 shows the antinociceptive effects of HM, BP, and biphalin in rats, and Table 3 shows levels of pain after implantation of HM+BP combined in one rod FIG. 2A shows levels of pain after intrathecal implantation of PLGA rods with hydrophone (HM), bupivacaine (BP), HM+BP, or with biphalin measured by paw withdrawal test (left side), and FIG. 2B shows levels of pain after intrathecal implantation of PLGA rods with hydrophone (HM), bupivacaine (BP), HM+BP, or with biphalin measured by paw withdrawal test (right side). Table 4 shows antinociceptive effects of placebo and HM delivered intrathecally in a PLGA rod; Table 5 shows the effects of BP and HM+BP deliverd in the same manner; and Table 6 shows the effects of biphalin.

Figure 3A:
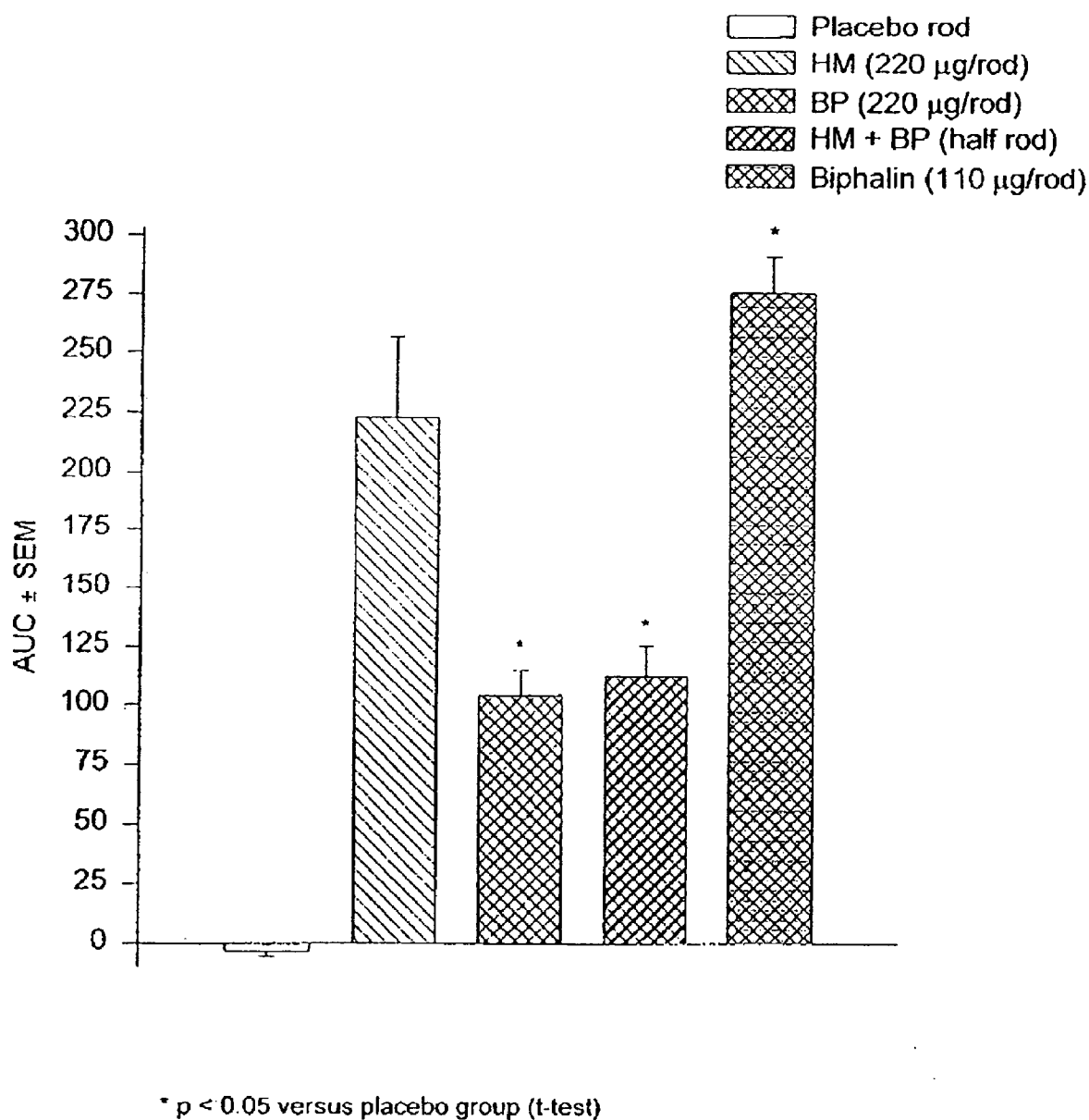
FIG. 3A is a bar graph showing area under curve (AUC) values for the aminociceptive effects of HM, BP, HM+BP, and biphalin form PLGA rods after intrathecal implantation to rats measured by tail flick test. $P<0.05$ versus placebo group (t-test)
Figure 3B:
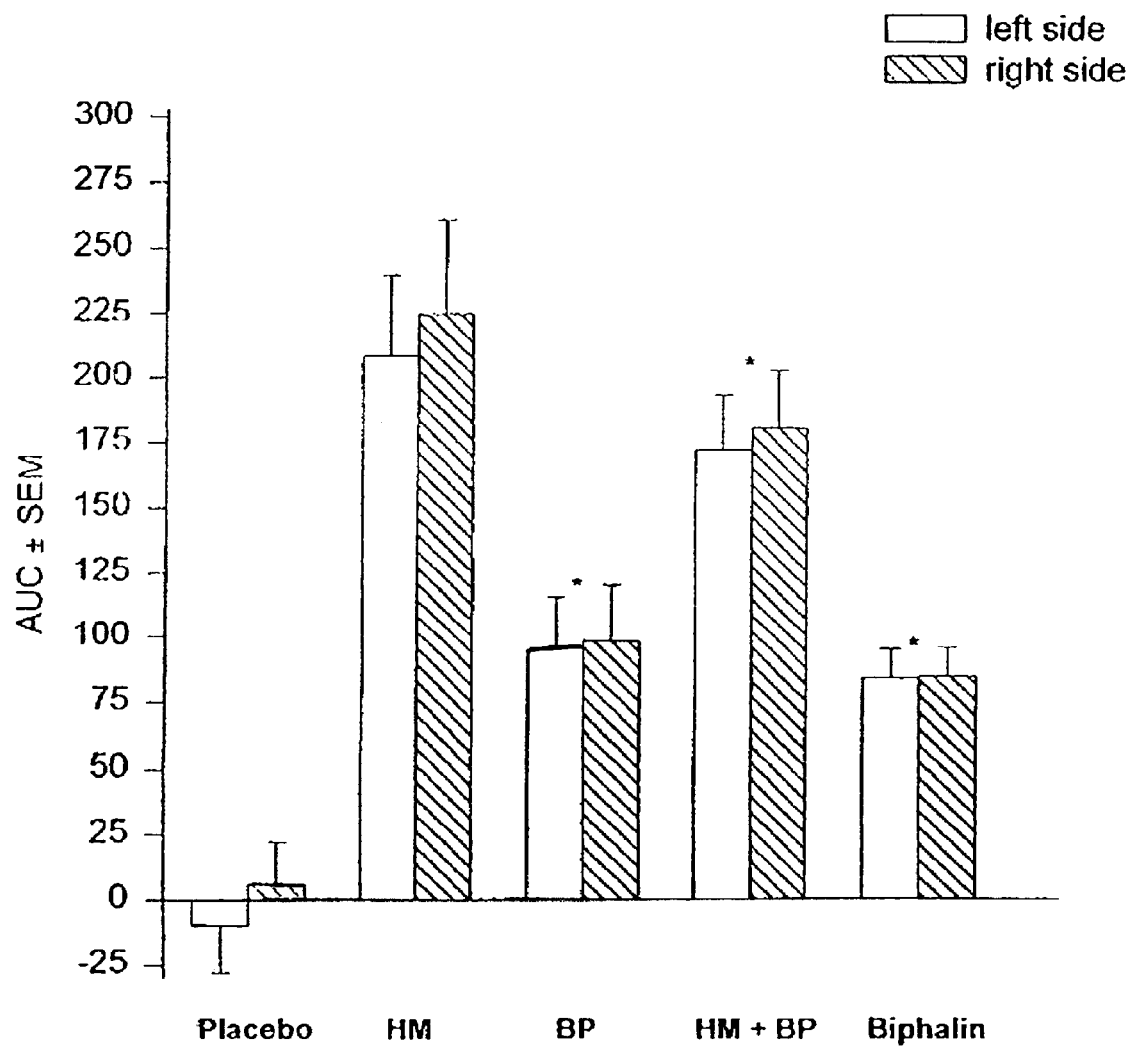
FIG. 3B is a bar graph showing AUC values for the aminociceptive effects of HM, BP, HM+BP, and biphalin form PLGA rods after intrathecal implantation to rats measured by paw withdrawal test. $P<0.05$ versus placebo group on the left and right side (t-test)

FIG. 3A shows AUC values for the aninociceptive effects of HM, BP, HM+BP, and biphalin form PLGA rods after intrathecal implantation to rats measured by tail flick test, and FIG. 3B shows AUC values for the aninociceptive effects of HM, BP, HM+BP, and biphalin form PLGA rods after intrathecal implantation to rats measured by paw withdrawal test. AUC values were calculated by a trapezoidal method for each group. Table 7 shows results using tail flick test; Table 8 shows results using the paw withdrawal test (left side); and Table 9 shows results using the paw withdrawal test (right side).

Figure 4:
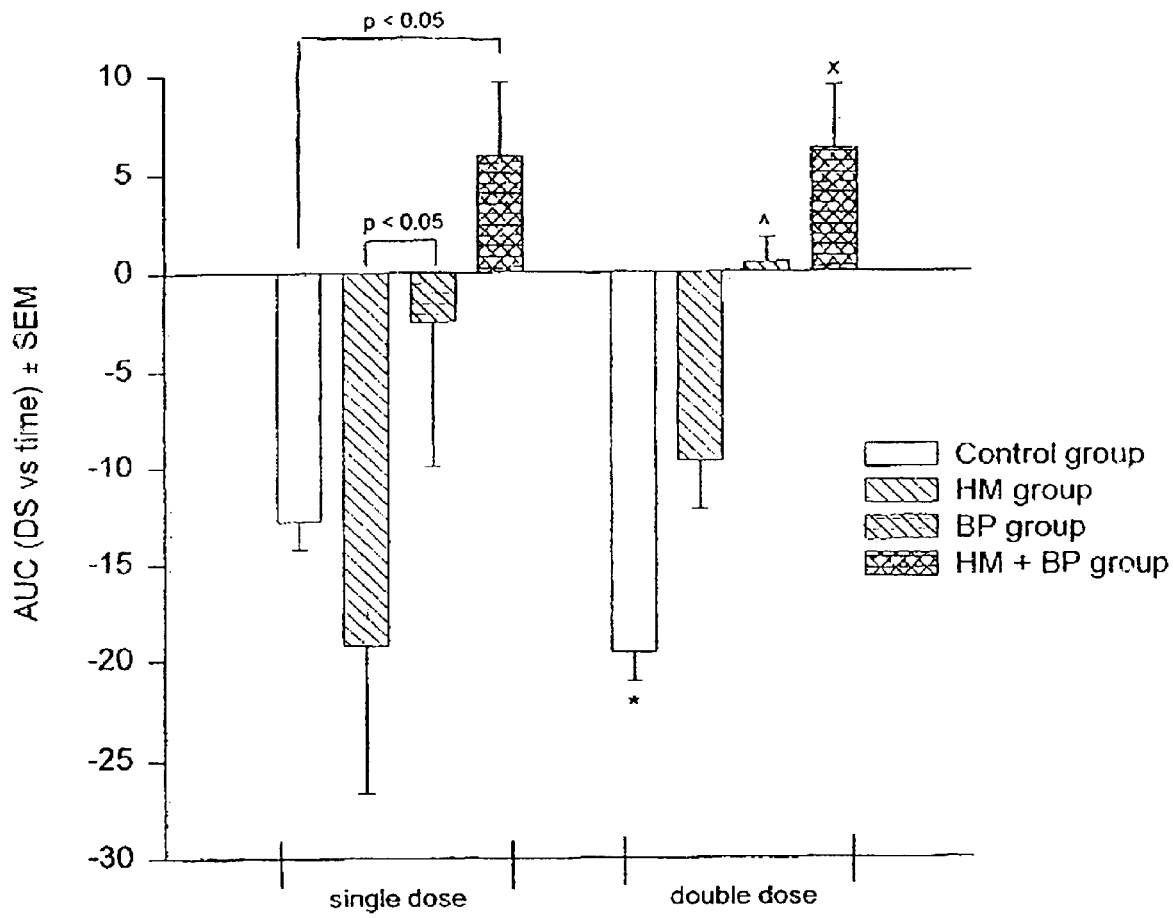
FIG. 4 is a bar graph showing AUC of the difference score (DS) versus time. In the study with rods containing single dose of 5 mg of HM or 5 mg of BP or 5 mg of HM+5 mg of BP were implanted in the site of sciatic nerve ligation on the right side. In the following part of the study, the number of implanted rods doubled, so rats received 10 mg of HM, or 10 mg of BP, or 10 mg of HM+4 mg of BP on the site of sciatic nerve ligation on the right side. Experimental groups included 6 rats. $P<0.05$ control group versus HM, BP, and HM+BP group. $P<0.05$ HM+BP group versus HM group and BP group. $P<0.05$ HM group versus BP group.

FIG. 4 shows AUC of the difference score (DS) versus time. In one study, rods containing a single dose of 5 mg HM, or 5 mg BP, or 5 mg HM and 5 mg BP together, were implanted int the site of sciatic nerve ligation on the right side. In a subsequent study the number of implanted rods doubled, so rats received 10 mg HM or 10 mg BP or 10 mg HM and 4 mg BP on the site of sciatic nerve ligation on the right side.

Simultaneous Controlled Release of Hydromorphone and Bupivacaine

A controlled drug delivery system consisting of a local anesthetic, bupivacaine (BP), and an analgesic, hydromorphone (HM) was designed and tested using a rat model for pain.

Rats were subjected to pain by constriction of their sciatic nerve of the right leg and drug release rods containing HM, or BP, or no drug were implanted to provide relief as measured by changes in their paw withdrawal thresholds. In vitro release from the rods were studied to predict their behavior in vivo. HPLC with electrochemical detectors and UV spectrophotometry were used for the determination of the drug content of the rods. Scanning electron microscopy was employed for obtaining morphological information.

It was possible to provide pain relief for prolonged periods with a single application a significant improvement over current application methods. The more effective pain relief with use of two different drugs simultaneously (the dual drug approach)

Among the opioid analgesics, morphine is the prototype and standard of comparison. Due to high solubilities and rapid excretion rates, morphine (or its derivatives) need to be taken frequently, such as every 4–6 h, with recurring pain at the beginning and the end of each period. HM is an oxidation product of morphine, and like morphine, it has a short half-life, and is 4–8 times more potent than morphine. It is used as an alternative to morphine by the oral and parenteral route in patients who require high doses or who have adverse reactions, such as histamine release, to morphine alone. Bupivacaine, on the other band, is a local anesthetic used for spinal and epidural analgesia, and provides excellent anesthesia with minimal impairment of motor function even with very low concentrations. It blocks motor axons, but the risk of hypotension is a possible concern especially after its epidural application. Local anesthetics used to provide single dose spinal anesthesia for surgery are supplemented with small doses of intrathecal opioid (eg. meperidine, fentanyl, morphine) to secure postoperative analgesia. After major surgery or trauma, epidural infusion of a combination of local anesthetic plus opioid is now the worldwide standard by which other methods of acute pain management are judged. The value of such combinations for movement-related pain has led to their adoption outside the acute care setting, for chronic management of cancer-related and non-malignant pain.

Spinal application of non-opioid agents plus opioid agents as described herein has only a dose-sparing, but also a tolerance impeding effect. Keeping the concentration of the local anesthetic low (eg. BP below 0.1%) minimizes the incidence of sensorimotor block during both acute and chronic infusion.

Although patients with intractable cancer pain had been studied previously during long term infusion of morphine and BP, this method was undertaken as a last resort for severe pain despite the absence of toxicity of this mixture to the meninges, nerve roots or spinal cord itself. Infusions of mixture were carried out via a subcutaneously tunnelled Portex nylon catheter. Long term co-infusions of BP and morphine were applied by both the epidural and subarachnoid routes for the treatment of refractory cancer pain achieved pain relief without clinically apparent signs of neurotoxicity. Other researchers demonstrated that combining extradural BP and fentanyl decreased analgesic requirements of each individual agent. Similarly both ketorolac and BP supplementation of HM patient-controlled epidural analgesia (PCEA) reduced the severities of pain on coughing and on movement compared with HM PCEA alone.

Patients who received postoperative analgesia via PCEA with sulfetanyl alone or with 0.06% or 0.12% BP and patients receiving BP had better pain relief than those receiving only the opioid. Morphine and BP used concomitantly intrathecal (i.t.) on 55 patients revealed that a single injection of i.t. morphine and BP provided rapid onset and effective analgesia with manageable side effects and without major complications. In a progressive cancer syndrome that involve the spinal cord and vertebrae, morphine and BP were intrathecally co-administered.

Simultaneous use of local anesthetics and opioids is an effective pain management approach. The implantable system described herein helps prevent patient immobilization and reduces expert care needed throughout the application.

The invention provides simultaneous delivery of local anesthetics and opioids, and optionally other agents as well, through implantable controlled release systems.

A biodegradable controlled release system of PLGA to release two drugs, HM and BP, simultaneously, was constructed Preparation of 25% BP or HM Loaded Rods of PLGA 50:50

To prepare PLGA 50:50 foam, polymer (8 g) (Resomer 506, BI Chemicals, Motvale, N.J.) was dissolved in glacial acetic acid (160 ml), frozen in isopropanol-dry ice bath for 1 h and then lyophilized overnight. Foam (1.50 g) was ground in a TEKMAR Model A-10 mill (Cincinnati, Ohio) and then sieved to obtain particles with diameters 45 mm. It was mixed with BP hydrochloride (Sigma Chemical Co., St. Louis, Mo.) or HM hydrochloride (Mallinekrodt Chemical Co., Chesterfield, Mo.) (0.5 g) and mixed on a ball mill for 2 h, before sieving to 45 mm and then re-grinding in TEKMAR mill. A steel mold equipped with a one inch rom and die with three 1.3 mm diameter holes was preheated at 55° C., the polymer-drug mixture was added, temperature increased to 65° C. and pressure of 15 tons was applied using a 40 ton hydraulic press (Compaq MPR40–1, Denmark). A small weight was attached to end of the extruded drug-polymer rod to prevent coiling. The resultant rods were ca. 20 mg in weight per cm.

In Vitro Release of BP or HM from PLGA Rods

A single drug rod (approximate length 1 cm, weight 20 mg) was placed in phosphate buffer saline (10 ml, 0.1M, pH 7.4) and introduced to shaking water bath (60 cycles/min) maintained at 37° C. The solution was changed every 24 h and the amount of drug was determined with UV spectrophotometry (Varian Cary 100) using the equations below (obtained from their calibration curves at the given wavelengths):

For BP hydrochloride (at lmax 262 nm)    A = 1.40669 C (mg/ml)
For HM hydrochloride (at lmax 280 nm)    A = 3.87613 C (mg/ml)

Scanning Electron Microscopy

Scanning electron micrographs of the drug-loaded rods (before and after in vivo tesing) were obtained after coating with gold or carbon (depending on the frailty of the sample).

In Vivo Testing

Experiments were performed on adult (205–275 g) male Sprague-Dawley rats housed in groups of three per cage in a controlled 12 hour light/12 hour dark environment. Animals had free access to food and water at all times.

The sciatic nerve ligation was done according to a standard methods. All rats received the surgical intervention, the right side was the treated side (ligation and rods placement), the left side remained untouched. At the time of surgery, rats were anesthetized with 3% isoflurane delivered via a nose cone. The right sciatic nerve was exposed at the level of the mid-thigh by blunt dissection through the biceps femoris. Approximately 10 mm of the nerve was freed of adhering tissue, and two 3-0 silk ligatures were tied loosely around the nerve with 1–2 mm between ligatures. The nerve was barely constricted when viewed under the microscope. Rods were placed parallel to the nerve and secured on place with loose ligature. The number of rods placed depended on the total dose of drugs chosen: two rods (in the first series of study) and four rods (in the second series of study). After the placement of the rods the incision was closed with 3-0 silk suture, and rats were allowed to recover from the general anesthesia. All animals postoperatively showed a mild eversion of the affected paw. Rats showed also a normal grooming behavior, and normal weight gain (weight gain was monitored every other day for the duration of experiment).

The rats were divided into four groups: control (received two polymer rods without drugs), and three treated groups: one received one rod with 2 mg of hydromorphone (HM) and one control rod, second—one rod with 2 mg of bupivacaine (BP) and one control rod, and third—one rod with 2 mg of HM and one rod 2 mg of with BP. In the second part of experiment the number of rods were doubled. All groups consisted of 6 rats.

The pain behavior assessment was performed using known methods. Unrestrained rats were placed in a clear plastic chamber (12.5×17×29 cm) with a glass floor and allowed to acclimate for approximatelly 15 minutes. Withdrawal responses to thermal stimulation were determined using 70 V source of visible light (emitted through a circular aperture of 4.5 mm diameter) which was placed 12 mm beneath a hind paw. Removal of the paw caused termination of the test and determined the pain threshold. The cut off time was established on 16 seconds to avoid paw damages. The testing was repeated 5 times for right and left hind paws with approximately 3–5 minutes between measurements. Rats were tested before the surgery (baseline threshold), and 1 hour and 2 hours after the rods placement. Day of surgery was considered the day 1 of experiment. Further testing was performed on day 2 and every other day for 12 days. Analgesia was expressed as a paw withdrawal threshold (sec), and as the area under the curve (AUC) of withdrawal threshold versus time. The data obtained during the paw withdrawal test were also presented as a difference score (DS) calculated from subtracting the treated (right) side from the control (left) side, and the area under the curve (AUC) of the difference score (DS) versus time. The negative DS indicates hyperalgesia. Data were analyzed by means of one way ANOVA and t-test to compare differences between groups. P value of <0.05 was considered statistically significant.

Blood samples were collected from each animal by nicking the tail before the rods placement and 3 hours later and then on the day 2, and on alternate days for 12 days. Blood samples (approximately 300–500 ml) were always drawn after the behavioral testing. After drawing, blood was left at room temperature to clot for 1 hour, and then was centrifuged at 9000 rpm for 6 minutes. The serum was collected and frozen at −80° C. until measurement of drug concentration by HPLC.

On the day 12, rats were euthanized with carbon dioxide, and the rods were removed and store at 4° C. until further testing for remaining contents of active agents.

Analysis of Rat Plasma for HM and BP

Serum (0.150 ml) and phosphate buffer saline (PBS, pH 74, 0.1M) were mixed in a 10 ml test tube. To this, internal standard naltrexone (50 ml, 0.2 mg/ml in methanol), HCl (650 ml, 0.1N) and benzene (3 ml) were added. This was vortexed for 1 min and the benzene layer (upper) discarded. Then sodium bicarbonate (300 ml, 1M) and benzene (3 ml) were added, vortexed for 1 min and the benzene layer was taken into a 12×75 mm disposable culture tube, evaporate to dryness in a vacuum oven at 45–50° C. This was then taken up in mobile phase (100 ml, pH 3.1, consisting of 12.5% v/v aqueous acetonitrile, 0.1M potassium dihydrogen phosphate and 0.5% w/v EDTA). This was transferred to 0.5 ml propylene centrifuge tubes for freezing at −20° C. After thawing it was centrifuged (2000 rpm, 5 min) before 30 ml was injected to a Waters HPLC (M-6000A) equipped with an electroanalytical cell (ESA, Model 5011), a detector (ESA Coulochem Model 5100A), and a Microsorb (MV86-200DS C 18, 5 mm, 100 Å) column, and a Hewlet-Packard (HP3390A) integrator. The peak areas were compared with that of the internal standard. The elution times for HM and naltrexone were 5.8 min and 23 min, respectively.

Determination of Drug Content of the Rods

After the removal of rods on the last (12 day) of experiment, every rod was placed in a test tube and 1 ml methylene chloride was added. Using a glass stirring rod the drug rod was crushed. HCl solution (2 ml, 0.1N, aqueous) was added and the tube was vortexed for one minute. The upper, HCl, layer was removed and a fresh HCl (2 ml) was added to the methylene chloride solution. It was extracted in the same fashion and the two top layers were combined before determining their drug contents with UV spectrophotometry using the above mentioned calibration data.

In Vitro Drug Release

In the in vitro release studies HM showed an almost first order behavior releasing almost all of its contents within a month. As such it was expected to release about 60% of its contents within the in vivo test duration of 12 days. BP rods on the other hand showed different behaviors in the two batches used. With the BP rods used in the first, low dose (a single rod was implanted), run release followed a zero order release pattern with two different rates; the rate of release was increased by a factor of two at around the 14th day. With these rods only about 35% of the drug content was released during the in vivo duration of 12 days. Since the rods were used up in the first run a new batch of BP rods were prepared. The zero order release pattern was, however, not followed in this second batch. The appearance this time was similar to first order, like that of HM but with a rate. Within the 12 day period ca. 80% of the drug was found in the release medium.

In Vivo Drug Release

HM rods used in the two in vivo runs were produced in the same batch, therefore, any variation in its release in between these runs is only the result of in vivo variability. The BP rods used in the tests, however, were produced (as explained above) in two different batches and had different release behaviors. The amount of drug released during the two in vivo tests are presented in Table 1.

TABLE 1

Drug released from HM or BP loaded rods retrieved after 12 days of implantation near rat sciatic nerve) (n = 3)

| Group | Drug | Single Dose Release (%, w/w) | Double Dose Release (%, w/w) |
|---|---|---|---|
| 1 | Hydromorphone | 68.37 ± 0.59 | 64.26 ± 6.37 |
| 2 | Bupivacaine | 27.68 ± 2.99 | 16.08 ± 8.56 |
| 3 | Hydromorphone | 67.18 ± 2.51 | 71.83 ± 2.11 |
|   | Bupivacaine | 16.59 ± 7.99 | 1.44 ± 3.66 |

(In the single dose application two rods were implanted into each rat (1 cm long, 1 mm in diameter, ca. 20 mg in weight) whereas this was doubled in the double dose case (4 rods/rat).

The amount of HM released in the in vivo medium closely followed its release in the in vitro tests. A 60% release was observed in the in vitro tests in 12 days and the 68.37% and 64.26% releases in the single and double dose applications, respectively, are very much in agreement with this result. Thus, about 3.4 mg and 6.4 mg of HM were delivered within 12 days. The 67.18% and 71.83% HM release in the dual drug applications releasing 3.4 mg and 7.2 mg of HM, respectively, are also very much in accordance with these values. As for the BP the results are not as clear cut. Even though the second batch appeared to release faster (35% vs 80% in 12 days), in the in vivo medium the second batch appeared to release less (27.68% vs 16.08%). This lowering was especially apparent when the dual drug application was employed (HM and BP rods used together). In the lower dose run the amount of BP released within 12 days dropped from 27.68% for single drug to 16.59% in dual drug application. In the higher dose case, the release of BP was substantially reduced (1.44%) as if its release was completely prevented by the high local dose of the acidic HM hydrochloride.

In Vivo Testing: Paw Withdrawal Threshold

The data obtained during the paw withdrawal test were presented as a difference score (DS) calculated from subtracting the treated (right) side from the control (left) side. The negative DS indicates hyperalgesia. In the first part of experiment when the implanted rods contained 2 mg of BP, 2 mg of HM we observed that the dose used in this group was insufficient to provide analgesia (indistinguishable from the control group). In the group of rats received combination of HM and BP analgesia reached sufficient level to elevate the pain threshold. The dual drug implanted animals however, had analgesia for almost the total duration of the 12 days. The untreated left tibia results of the same animals indicate that the values are quite close to one another and to zero. The dual drug implanted animal's left leg also showed an analgesic response but for a shorter duration and at a lower level.

When the dose of the drug was doubled using twice as much rods as before, it was possible to achieve the analgesic effect even in the single type of drug (HM or BP) implanted animals. Here, the placebo was distinctly lower throughout the test than the others. Dual drug caused the highest effect followed by initially BP and later by HM. These are quite expected because while BP is a local anesthetic and should show its effect immediately, HM acts systemically and thus takes longer to be active. The untreated tibia showed values quite close to baseline (after an initial insensitivity) and thus prove that the results are reproducible. The distinct difference between the response of the dual drug implanted animals and the animals implanted with a single type of drug could be simply due to the dose applied. To check that, data for all the animals implanted with the double dose were plotted alongside the dual drug of the single dose application. Here, it was also observed that both dual doses are higher than any of the double dose HM and BP implying an effect (such as synergism) different than that of dose.

Scanning Electron Microscopy

The unused rods all appeared to have a smooth, hole-free skin layer regardless of whether they contained a drug or not. The appearance within the rod, however, was very different when it contained a drug than when it did not. The drug appeared to be localized as a different phase or as a solid solution of drug in the polymer matrix surrounded by a dense skin layer. Upon implantation even though the surfaces appear hole-free, the cross-sections revealed deep reaching pores, the sizes of which appear to be larger as the central axis of the rod is approached. This probably is caused by the extrusion process through which the rods are produced. The polymer on the exterior of the rod which is in contact with the die flows because the temperature is above its Tg and this skin layer becomes denser than the center. Thus, the release of drugs is probably through dissolution, and permeation through the skin layer. The burst observed is probably because of the leaching of the drug particles entrapped in the skin layer. Later release is due to both permeation through the skin as well as through the pores created by the leaching of particles embedded in the skin.

Currently available local anesthetics and opioid analgesics have a relatively limited duration of activity (due to their short plasma half-lives) and some may cause severe toxicity due to their low LD50 values. Prolongation of action would significantly benefit the patients, help use less drug, lower toxicity, and development of tolerance might also be more gradual. The recent trend in pain management involved coupling of two drugs, one a local anesthetic and the other an opioid for more effective pain management to achieve rapid and long-term relief with the use of less analgesics.

The applications along this direction involved continuous i.v. or i.t. administrations to prolong the duration and is an approach that immobilizes the patients, leads to pain, requires patient compliance and continual care by professionals. In a very successful example of such an application Dahm et al (1998) used long term, continuous intrathecal (i.t.) opioid (buprenorphine 0.015 mg/ml, 0.114 mg/day) and bupivacaine (bupivacaine 4.75 mg/ml, 37 mg/day) analgesia in a case not amendable to corrective surgery due to the absence of any reliable method for long-term (more than 6 years) treatment of severe pain following complications of hip arthroplasty. This dual, i.t. treatment gave the patient 85–100% relief and mobility to carry out everyday activities.

Continuous s.c. infusion using portable infusion pumps appears to carry all the advantages of continuous i.v. infusion with the added benefits of greater mobility, management on an outpatient basis, and avoidance of the need for i.v. access (Moulin et al, 1991).

Long term co-infusions of bupivacaine and morphine were applied by both the epidural and subarachnoid routes for the treatment of refractory cancer pain achieved pain relief without clinically apparent signs of neurotoxicity.

Similarly both ketorolac and bupivacaine supplementation of hydromorphone patient-controlled epidural analgesia (PCEA) reduced the severities of pain on coughing and on movement compared with hydromorphone PCEA alone.

Morphine and bupivacaine used concomitantly intrathecal (i.t.) on 55 patients revealed that a single injection of i.t. morphine and bupivacaine provided rapid onset and effective analgesia with manageable side effects and without major complications. Infusion is, still, a restricting mode of application. Continuous provision of drugs without being continuously connected to catheters is very important. Sustained release systems provide this mobility. Codeine Contin in sustained release (150 mg/12 h) form was found to be equianalgesic to much higher doses of acetaminophen+ codeine (600 mg+60 mg/6 h). Even in this application the administration frequency is quite short (12 h).

Still a controlled release form of hydromorphone was prepared with 12 h activity to prolong half-life and improve patient compliance as in the case of MS and Codeine Contin. This form was highly effective in the treatment of chronic, severe cancer pain.

Polymeric carriers were able to provide longer term releases. A typical example of these is the use of PLGA mainly in the form of microspheres. For example, PLGA was used to carry a combination of drugs (but not both analgesics). PLGA 65:35 microspheres loaded with 75% w/w bupivacaine alone or with 0.05% w/w dexamethasone were injected into rats and produced sciatic nerve block for 10–5.5 days as shown with thermal sensory testing as well as motor testing. The presence of dexamethasone increased the block duration ca. 13-fold attesting to the possibility of increasing the duration of activity by the use of a combination of drugs, and the potential value of decreasing local inflammation.

Bupivacaine loaded poly(d,l-lactic acid) microspheres were introduced to rabbits via a chronically implanted epidural catheter. Significant delay in reaching maximum effects and prolongation of motor block (244%) were observed. Microspheres, due to their large surface area and small size, generally tend to release rapidly and are hard to localize.

EXAMPLE 2
Intrathecal Polymeric Implants

PLGA rods were prepared by converting polymer to a foam, which was ground, sieved and mixed overnight with drug. The PLGA was formulated as a 85:15 copolymer. The polymer-drug mix was extruded under pressure. Rods were introduced intrathecally into rats using a silicone catheter. Release of HM, BP, and biphalin was studied.

Drug release studies showed that BP was released faster than the other two drugs with HM being the slowest. Release was almost zero order for BP and HM. Biphalin release occurred in two phases.

Initial implantations of HM rods showed steady anesthesia (compared to i.t. placebo) lasting 3–4 days and decreasing thereafter to all sites tested. The degree of anesthesia was highest 2 hours after implantation. BP rods produced continuous anesthesia for at least 4 days.

Dual rods contained 5% HM and 2.5% BP and showed almost 100% anesthesia on the first day, decreasing to 20% on the third day. This result when compared with HM or BP alone indicated synergistic anesthesia, because the dual rod contained ½ and ¼ of the amount of HM and BP of the individual rods.

Biphalin i.t. rods had an analgesic profile different from HM and BP type drugs. Analgesia exceeded each of the single rods in the first day having a half loading of the drug (5%), decreasing on the second day, and continuing for about 3 days.

The strong synergy observed with dual drug rods indicated that this approach is advantageous for severe pain due to the high efficacy obtained with decreased amounts of drug.

The compositions and methods described herein provide a long term, controllable approach to drug delivery, e.g., for alleviation of pain. The in vitro release behavior of the rods revealed that a release for at least 12 days is possible with a release behavior between Zero order and first order because even though the rods were monolithic in composition the extrusion process probably lead to a rate control membrane layer as was seen in the SEM. In vivo data contained both detection of paw withdrawal threshold as a measure of effectiveness of pain management and also the drug content in the rods remaining after an experimental test period of 12 days. Rods containing mg quantities of drug (e.g., greater than 5 mg, 10 mg, 15 mg, 20 mg) are effective to provide relief from pain for several days (e.g., 2, 3, 5, 10, 15, or more days).

TABLE 2

Antinociceptive efftects of hydromorphone, bupivacaine and biphalin in rats deliverd intrathecally in the PLGA rod measured by the tail flick test 2.4 hours and for next 6 days after implantation

| % MPE | 2h | 4h | D1 | D2 | D3 | D4 | D5 | D6 |
|---|---|---|---|---|---|---|---|---|
| Placebo (control rod) | | | | | | | | |
| Rat 1 | 2.997275 | 1.089918 | 1.3624 | 0.817439 | −0.81744 | −0.81744 | 1.362398 | −1.63488 |
| Rat 2 | 0.280112 | 0.560224 | 1.680672 | −0.28011 | −1.12045 | −1.40056 | −0.28011 | −0.84034 |
| Rat 3 | 1.94444 | −1.66667 | −1.66667 | 0.277778 | −2.5 | −2.5 | −0.55556 | −1.38889 |
| Rat 4 | 2.173913 | 1.358696 | 1.630435 | 1.63043 | −0.81522 | −0.27174 | 0.271739 | −0.27174 |
| Rat 5 | 3.055556 | 0.833333 | −3.05556 | −2.77778 | −2.22222 | −2.22222 | −0.55556 | −1.38889 |
| Rat 6 | 3.030303 | 0.826446 | 3.030303 | 1.652893 | 0.275482 | −1.10193 | −1.92837 | −1.65289 |
| Average | 1.598786 | 0.500325 | 0.042798 | −0.32337 | −1.19997 | −1.38565 | −0.28091 | −1.19627 |
| Standard deviation | 2.037221 | 1.095547 | 2.392699 | 1.631125 | 1.021051 | 0.846878 | 1.083594 | 0.539728 |
| Standard error | 0.831692 | 0.447255 | 0.976815 | 0.665901 | 0.416842 | 0.345736 | 0.442375 | 0.220343 |
| Hydromorphone (HM – 220 μg/rod) | | | | | | | | |
| Rat 1 | 100 | 91.41825 | 79.9458 | 50.67751 | 50.67751 | 47.96748 | 29.26829 | 19.5122 |
| Rat 2 | 100 | 76.21483 | 100 | 84.39898 | 44.24552 | 44.24552 | 30.94629 | 13.04348 |
| Rat 3 | 80.2168 | 56.09756 | 70.4607 | 42.00542 | 36.58537 | 18.69919 | 13.82114 | 9.214092 |
| Rat 4 | 45.73003 | 49.03581 | 49.31129 | 48.20937 | 18.73278 | 8.539945 | 1.37741 | 0 |
| Rat 5 | 44.71545 | 38.48238 | 61.24661 | 30.89431 | 27.10027 | 17.07317 | 1.355014 | −0.81301 |
| Rat 6 | 48.54881 | 50.39578 | 44.06332 | 55.14512 | 29.02375 | 23.48285 | 3.693931 | −0.5277 |
| Average | 69.86851 | 60.2741 | 67.50462 | 51.88845 | 34.3942 | 26.66803 | 13.41035 | 6.738175 |
| Standard deviation | 26.80587 | 19.69907 | 20.68393 | 18.00539 | 11.78405 | 15.85542 | 13.73815 | 8.535561 |
| Standard error | 10.94345 | 8.042113 | 8.44418 | 7.35067 | 4.810818 | 6.472948 | 5.608576 | 3.484628 |
| Bupivacaine (BP) 220 μg/rod | | | | | | | | |
| Rat 1 | 31.18557 | 24.2268 | 14.94845 | 13.40206 | 14.94845 | 14.43299 | 9.536082 | 8.247423 |
| Rat 2 | 41.43223 | 38.87468 | 27.10997 | 32.22506 | 22.50639 | 14.0665 | 4.092072 | 0.767263 |
| Rat 3 | 63.07692 | 40.25641 | 31.79487 | 40.51282 | 26.92308 | 7.948718 | 7.692308 | 7.948718 |
| Rat 4 | 30.89005 | 44.7644 | 25.65445 | 16.49215 | 13.87435 | 5.235602 | 5.235602 | 8.115183 |
| Rat 5 | 23.84615 | 11.79487 | 11.53846 | 13.33333 | 18.46154 | 12.5641 | 7.948718 | 7.179487 |

TABLE 2-continued

Antinociceptive efftects of hydromorphone, bupivacaine and biphalin in rats deliverd intrathecally
in the PLGA rod measured by the tail flick test 2.4 hours and for next 6 days after implantation

| % MPE | 2h | 4h | D1 | D2 | D3 | D4 | D5 | D6 |
| --- | --- | --- | --- | --- | --- | --- | --- | --- |
| Rat 6 | 52.68817 | 74.46237 | 27.95699 | 19.35484 | 23.11828 | 9.946237 | 15.86022 | 0.806452 |
| Average | 40.51985 | 39.06325 | 23.1672 | 22.55338 | 19.97201 | 10.69902 | 8.394166 | 5.510754 |
| Standard deviation | 14.93718 | 21.21671 | 8.023541 | 11.24107 | 5.086032 | 3.653512 | 4.152624 | 3.677823 |
| Standard error | 6.098076 | 8.661686 | 3.275597 | 4.589147 | 2.076364 | 1.49154 | 1.695302 | 1.501465 |

TABLE 3

| % MPE | 2h | 4h | D1 | D2 | D3 | D4 | D5 | D6 |
| --- | --- | --- | --- | --- | --- | --- | --- | --- |
| Hydromorphone + Bupivacaine (HM + BP) combined in one rod (220 μg/rod of each) - half rod was implanted | | | | | | | | |
| Rat 1 | 69.68085 | 67.55319 | 23.1383 | 40.69149 | 23.1383 | 19.41489 | 11.17021 | 0.797872 |
| Rat 2 | 68.27957 | 65.86022 | 24.46237 | 33.60215 | 18.01075 | 14.51613 | 5.376344 | −0.26882 |
| Rat 3 | 56.95187 | 57.75401 | 16.04278 | 11.22995 | 19.25134 | −1.06952 | 4.010695 | −3.20856 |
| Rat 4 | 57.29443 | 55.96817 | 28.11671 | 21.22016 | 6.100796 | −0.5305 | 2.122016 | −1.32626 |
| Rat 5 | 100 | 100 | 37.53281 | 42.25722 | 6.824147 | 3.149606 | 4.199475 | −3.67454 |
| Rat 6 | 71.96765 | 67.38544 | 19.40701 | 16.71159 | 16.44205 | 15.63342 | 4.043127 | −1.88679 |
| Average | 70.69573 | 69.08684 | 24.78333 | 27.61876 | 14.96123 | 8.519005 | 5.153645 | −1.59452 |
| Standard deviation | 15.72078 | 15.94875 | 7.506954 | 13.03444 | 6.949551 | 9.032881 | 3.126963 | 1.707045 |
| Standard error | 6.417981 | 6.511052 | 3.064701 | 5.321288 | 2.837142 | 3.687658 | 1.276577 | 0.696898 |
| Biphalin (110 μg/rod) | | | | | | | | |
| Rat 1 | 80 | 85.6 | 84.8 | 73.6 | 32.53333 | 22.66667 | 9.066667 | 10.4 |
| Rat 2 | 96.45777 | 83.65123 | 71.9346 | 73.297 | 35.14986 | 20.16349 | 12.26158 | 5.177112 |
| Rat 3 | 86.99187 | 91.59892 | 75.88076 | 69.9187 | 36.58537 | 31.16531 | 21.13821 | 4.065041 |
| Rat 4 | 84.65608 | 100 | 100 | 90.47619 | 73.54497 | 33.33333 | 3.174603 | 2.380952 |
| Rat 5 | 76.48649 | 88.91892 | 72.97297 | 55.13514 | 50.27027 | 21.08108 | 1.081081 | −4.32432 |
| Rat 6 | 95.43011 | 100 | 87.63441 | 76.34409 | 53.49462 | 15.5914 | 7.795699 | −5.64516 |
| Average | 86.67039 | 91.62818 | 82.20379 | 73.12852 | 46.92974 | 24.00021 | 9.086307 | 2.008937 |
| Standard deviation | 8.06092 | 7.035431 | 10.80354 | 11.36307 | 15.59266 | 6.843597 | 7.155819 | 6.058195 |
| Standard error | 3.290857 | 2.872203 | 4.410525 | 4.638955 | 6.365678 | 2.793887 | 2.921351 | 2.473248 |

TABLE 4

Antinociceptive effects of hydromorphone, bupivacaine and biphalin in rats delivered
intrathecally in the PLGA rod measured by the paw withdrawal test 2, 4 hours and
for next 6 days after implantation (on the left (L) and right (R) hind paw)

| | 2h | | 4h | | D1 | | D2 | |
| --- | --- | --- | --- | --- | --- | --- | --- | --- |
| % MPE | L | R | L | R | L | R | L | R |
| Placebo (control rod) | | | | | | | | |
| Rat 1 | 13.98 | 17.40 | −7.10 | 0.63 | 10.54 | 12.37 | 13.98 | 14.05 |
| Rat 2 | −25.25 | −23.19 | −14.65 | −6.76 | −6.06 | −0.97 | −11.11 | −3.38 |
| Rat 3 | −13.57 | −18.32 | 3.52 | 9.41 | −25.63 | −24.75 | −9.04 | −8.42 |
| Rat 4 | 2.90 | 5.22 | −2.49 | −0.43 | 12.45 | 11.30 | −3.32 | −5.65 |
| Rat 5 | 1.68 | 5 | 2.52 | 5.83 | 5.88 | 5.83 | 3.78 | 6.67 |
| Rat 6 | 10.92 | 14.28 | −11.35 | −6.30 | −2.62 | 3.36 | −7.86 | −2.10 |
| Average | −1.56 | 0.07 | −4.92 | 0.39 | −0.91 | 1.19 | −2.26 | 0.19 |
| Standard deviation | 15.05 | 16.92 | 7.39 | 6.44 | 14.11 | 13.65 | 9.56 | 8.49 |
| Standard error | 6.14 | 6.91 | 3.02 | 2.63 | 5.76 | 5.57 | 3.90 | 3.46 |
| Hydromorphone (HM - 220 μg/rod) | | | | | | | | |
| Rat 1 | 100 | 100 | 79.75 | 81.93 | 88.18 | 90.76 | 87.76 | 80.32 |
| Rat 2 | 100 | 66.41 | 49.62 | 50.58 | 70.77 | 85.33 | 60.38 | 62.55 |
| Rat 3 | 55.80 | 54.96 | 49.28 | 56.03 | 68.48 | 67.37 | 77.90 | 72.34 |
| Rat 4 | 29.54 | 25.82 | 11.36 | 15.64 | 31.82 | 40.36 | 35.98 | 42.18 |
| Rat 5 | 38.75 | 34.86 | 27.34 | 25 | 39.79 | 36.62 | 29.06 | 23.24 |

TABLE 4-continued

Antinociceptive effects of hydromorphone, bupivacaine and biphalin in rats delivered intrathecally in the PLGA rod measured by the paw withdrawal test 2, 4 hours and for next 6 days after implantation (on the left (L) and right (R) hind paw)

| | | | | | | | | |
|---|---|---|---|---|---|---|---|---|
| rat 6 | 39.02 | 42.32 | 39.84 | 23.65 | 34.15 | 36.10 | 41.87 | 45.23 |
| Average | 60.52 | 54.06 | 42.86 | 42.14 | 55.53 | 59.42 | 55.49 | 54.31 |
| Standard deviation | 31.73 | 26.71 | 23.19 | 25.24 | 23.38 | 25.07 | 23.80 | 21.28 |
| Standard error | 12.95 | 10.91 | 9.47 | 10.30 | 9.54 | 10.24 | 9.72 | 8.69 |

| | D3 | | D4 | | D5 | | D6 | |
|---|---|---|---|---|---|---|---|---|
| % MPE | L | R | L | R | L | R | L | R |
| Placebo (control rod) | | | | | | | | |
| Rat 1 | 7.10 | 11.11 | 14.41 | 18.66 | 5.38 | 5.24 | 16.99 | 16.98 |
| Rat 2 | −13.13 | −0.48 | −9.60 | −1.93 | −4.54 | 0.97 | −9.56 | −1.93 |
| Rat 3 | −14.57 | −7.92 | −1.01 | 2.97 | −10.05 | −6.44 | −0.50 | 1.98 |
| Rat 4 | −1.66 | −5.65 | 2.90 | −2.61 | 1.24 | −4.78 | 3.73 | −4.78 |
| Rat 5 | 3.78 | 5.83 | 2.10 | 8.75 | 0 | 4.17 | 0.84 | 2.08 |
| Rat 6 | −3.93 | −0.84 | −3.93 | −2.94 | −3.49 | −3.78 | −3.06 | 0 |
| Average | −3.74 | 0.34 | 0.81 | 3.82 | −1.91 | −0.77 | 1.40 | 2.39 |
| Standard deviation | 8.76 | 7.11 | 8.06 | 8.55 | 5.34 | 4.92 | 8.87 | 7.60 |
| Standard error | 3.58 | 2.90 | 3.29 | 3.49 | 2.18 | 2.01 | 3.62 | 3.10 |
| Hydromorphone (HM - 220 μg/rod) | | | | | | | | |
| Rat 1 | 54.85 | 68.67 | 39.66 | 31.73 | 1.69 | 5.62 | −12.24 | 0 |
| Rat 2 | 58.85 | 54.83 | 35 | 35.91 | 12.69 | 13.90 | −12.31 | −12.36 |
| Rat 3 | 45.29 | 67.38 | 36.23 | 51.77 | 21.74 | 36.17 | 9.78 | 12.76 |
| Rat 4 | 33.71 | 31.64 | 32.20 | 37.09 | 13.25 | 17.45 | −0.76 | 4 |
| Rat 5 | 35.64 | 34.51 | 18.68 | 25.35 | 15.22 | 17.96 | 16.61 | 19.37 |
| rat 6 | 16.26 | 16.60 | 12.60 | 9.13 | −1.22 | −0.83 | −6.91 | −8.71 |
| Average | 40.77 | 45.60 | 29.06 | 31.83 | 10.56 | 15.04 | −0.97 | 2.51 |
| Standard deviation | 15.64 | 21.22 | 10.84 | 14.14 | 8.67 | 12.67 | 11.96 | 12.20 |
| Standard error | 6.38 | 8.66 | 4.42 | 5.77 | 3.54 | 5.17 | 4.88 | 4.98 |

TABLE 5

| | 2h | | 4h | | D1 | | D2 | |
|---|---|---|---|---|---|---|---|---|
| % MPE | L | R | L | R | L | R | L | R |
| Bupivacaine (BP - 220 μg/rod) | | | | | | | | |
| rat 1 | 19.26 | 20.77 | 11.48 | 13.08 | 11.11 | 11.54 | 18.15 | 15.77 |
| rat 2 | 23.67 | 27 | 14.67 | 12 | 39 | 32 | 29 | 28.33 |
| rat 3 | 15.95 | 22.43 | 37.74 | 44.11 | 13.62 | 11.03 | 33.07 | 34.60 |
| rat 4 | 36.73 | 38.63 | 11.64 | 11.91 | 8.36 | 7.58 | 9.45 | 11.19 |
| rat 5 | 24.92 | 19.06 | 27.69 | 38.12 | 33.85 | 30.62 | 28.92 | 28.12 |
| rat 6 | 36.09 | 39.35 | 55.64 | 58.84 | 35.71 | 43.32 | 42.86 | 44.76 |
| Average | 26.10 | 27.87 | 26.48 | 29.68 | 23.61 | 22.68 | 26.91 | 27.13 |
| Standard deviation | 8.60 | 9.01 | 17.68 | 20.17 | 13.98 | 14.59 | 11.68 | 12.27 |
| Standard error | 3.51 | 3.68 | 7.22 | 8.23 | 5.71 | 5.96 | 4.77 | 5.01 |
| Hydromorphone + Bupivacaine (HM + BP) combined in one rod (220 μg/rod of each) - half rod was implanted | | | | | | | | |
| rat 1 | 100 | 100 | 100 | 100 | 54.64 | 51.81 | 52.5 | 53.62 |
| rat 2 | 100 | 97.38 | 77.98 | 87.64 | 76.12 | 70.79 | 28.73 | 23.60 |
| rat 3 | 100 | 100 | 100 | 100 | 58.31 | 63.19 | 44.41 | 50.16 |
| rat 4 | 100 | 100 | 90.42 | 87.76 | 33.69 | 36.01 | 37.59 | 34.96 |
| rat 5 | 95.68 | 100 | 99.34 | 100 | 45.85 | 52.96 | 25.91 | 33.55 |
| rat 6 | 76.22 | 68.73 | 62.24 | 68.04 | 43.36 | 37.11 | 14.34 | 15.81 |
| Average | 95.32 | 94.35 | 88.33 | 90.57 | 51.99 | 51.98 | 33.91 | 35.28 |
| Standard deviation | 9.51 | 12.60 | 15.40 | 12.58 | 14.67 | 13.83 | 13.73 | 14.67 |
| Standard error | 3.88 | 5.14 | 6.27 | 5.13 | 5.99 | 5.65 | 5.61 | 5.99 |

TABLE 5-continued

| % MPE | D3 | | D4 | | D5 | | D6 | |
|---|---|---|---|---|---|---|---|---|
| | L | R | L | R | L | R | L | R |
| Bupivacaine (BP - 220 μg/rod) | | | | | | | | |
| rat 1 | 20.37 | 17.31 | 7.78 | 8.46 | 0.74 | 0.38 | 0.37 | 0.77 |
| rat 2 | 7.33 | 4.67 | 13.67 | 15.67 | 1 | 3 | 7 | 11 |
| rat 3 | 9.73 | 12.55 | 1.55 | 0.76 | 1.94 | 2.66 | 0.39 | 4.94 |
| rat 4 | 5.09 | 0.36 | 0 | 1.08 | 1.45 | 1.44 | −1.82 | 2.89 |
| rat 5 | 16.62 | 24.69 | 25.54 | 20.94 | 18.77 | 18.44 | 10.15 | 9.69 |
| rat 6 | 31.20 | 34.66 | 9.77 | 10.47 | 15.04 | 13.36 | 13.16 | 14.80 |
| Average | 15.06 | 15.70 | 9.72 | 9.56 | 6.49 | 6.55 | 4.88 | 7.35 |
| Standard deviation | 9.78 | 12.72 | 9.28 | 7.98 | 8.16 | 7.48 | 6.10 | 5.35 |
| Standard error | 3.99 | 5.20 | 3.79 | 3.26 | 3.33 | 3.05 | 2.49 | 2.18 |
| Hydromorphone + Bupivacaine (HM + BP) combined in one rod (220 μg/rod of each) - half rod was implanted | | | | | | | | |
| rat 1 | 45.36 | 42.39 | 18.93 | 21.74 | 15.71 | 10.87 | 6.78 | 4.35 |
| rat 2 | −0.75 | −1.12 | 6.72 | 6.37 | 12.31 | 15.73 | 14.55 | 14.23 |
| rat 3 | 27.12 | 37.78 | 23.05 | 26.06 | 10.85 | 13.03 | 6.44 | 2.28 |
| rat 4 | 23.76 | 28.67 | 15.60 | 18.88 | 7.80 | 10.49 | 0.35 | 6.29 |
| rat 5 | 22.26 | 23.36 | 12.62 | 13.82 | 14.95 | 20.72 | 4.65 | 8.55 |
| rat 6 | 2.80 | 6.18 | 5.59 | 6.87 | −3.85 | −2.41 | −9.79 | −9.28 |
| Average | 20.09 | 22.88 | 13.75 | 15.62 | 9.63 | 11.41 | 3.83 | 4.40 |
| Standard deviation | 16.96 | 17.27 | 6.84 | 8.03 | 7.20 | 7.75 | 8.11 | 7.86 |
| Standard error | 6.93 | 7.05 | 2.79 | 3.28 | 2.90 | 3.16 | 3.31 | 3.21 |

TABLE 6

| % MPE | 2h | | 4h | | D1 | | D2 | | D3 | |
|---|---|---|---|---|---|---|---|---|---|---|
| | L | R | L | R | L | R | L | R | L | R |
| Biphalin (110 μg/rod) | | | | | | | | | | |
| rat 1 | 100 | 100 | 100 | 100 | −1.89 | −2.32 | −5.68 | −6.20 | 12.12 | 9.30 |
| rat 2 | 100 | 100 | 100 | 100 | 10.92 | 10.84 | 12.97 | 9.44 | 17.06 | 13.64 |
| rat 3 | 100 | 100 | 100 | 100 | 18.44 | 16.61 | 20.92 | 16.61 | 12.06 | 11.07 |
| rat 4 | 100 | 100 | 100 | 100 | 21.78 | 25.27 | 13.93 | 11.03 | −4.64 | −1.07 |
| rat 5 | 100 | 100 | 100 | 100 | 30.27 | 38.69 | 6.46 | 4.92 | −2.04 | 7.54 |
| rat 6 | 100 | 100 | 100 | 100 | 7.30 | 10.29 | 1.46 | 0.37 | 10.58 | 9.92 |
| Average | 100 | 100 | 100 | 100 | 14.47 | 16.56 | 8.34 | 6.03 | 7.52 | 8.40 |
| Standard deviation | 0 | 0 | 0 | 0 | 11.41 | 14.10 | 9.58 | 8.14 | 8.74 | 5.06 |
| Standard error | 0 | 0 | 0 | 0 | 4.61 | 5.76 | 3.91 | 3.32 | 3.57 | 2.07 |

| % MPE | D4 | | D5 | | D6 | |
|---|---|---|---|---|---|---|
| | L | R | L | R | L | R |
| Biphalin (110 μg/rod) | | | | | | |
| rat 1 | 2.27 | −0.78 | 18.18 | 21.32 | 14.39 | 15.89 |
| rat 2 | 11.94 | 9.44 | 15.02 | 17.48 | 2.73 | 2.45 |
| rat 3 | 2.84 | 2.21 | 2.13 | 0.37 | −0.35 | −3.32 |
| rat 4 | 2.14 | −2.14 | −5 | −2.49 | −5.71 | −5.34 |
| rat 5 | 0.34 | 3.28 | 4.42 | 8.52 | −0.68 | 0.98 |
| rat 6 | −8.39 | −5.88 | −14.60 | −16.91 | −7.66 | −10.6 |
| Average | 1.86 | 1.02 | 3.36 | 4.72 | 0.45 | 0.00 |
| Standard deviation | 6.49 | 5.26 | 12.25 | 14.08 | 7.82 | 9.08 |
| Standard error | 2.65 | 2.15 | 5.00 | 5.75 | 3.19 | 3.71 |

Area under the curve (AUC) values (calculated by a trapezoidal method) for each group of rats received intrathecal control (placebo) rod or rod with hydromorphone (HM), bupivacaine (BP), hydromorphone plus bupivacaine (HM+BP) or with biphalin measured in the

TABLE 7

Tail flick test:

| rat | Placebo | HM | BP | HM + BP | Biphalin |
|---|---|---|---|---|---|
| 1 | −0.90 | 307.95 | 82.59 | 149.95 | 263.66 |
| 2 | −1.68 | 341.41 | 112.23 | 126.91 | 251.97 |
| 3 | −8.36 | 209.55 | 137.33 | 75.41 | 276.26 |
| 4 | −0.37 | 146.61 | 90.32 | 82.15 | 343.10 |
| 5 | −10.79 | 151.85 | 72.88 | 139.12 | 236.51 |
| 6 | 1.36 | 176.73 | 130.77 | 103.61 | 280.84 |
| Mean | −3.46 | 222.35 * | 104.35 * # | 112.86 * # ^ | 275.39 * |
| Standard error | 2.00 | 33.89 | 10.81 | 12.51 | 15.07 |
| Standard deviation | 4.90 | 83.01 | 26.49 | 30.64 | 36.91 |

\* $p < 0.05$ group HM, BP, HM + BP, biphalin vs placebo group (t-test)
\# $p < 0.05$ group HM vs group BP and HM + BP,
^ $p < 0.05$ group BP vs group HM + BP (t-test)

TABLE 8

Paw withdrawal test (left side):

| Rat | Placebo | HM | BP | HM + BP | Biphalin |
|---|---|---|---|---|---|
| 1 | 56.36 | 299.65 | 63.50 | 236.16 | 82.35 |
| 2 | −56.50 | 252.70 | 98.08 | 164.19 | 118.40 |
| 3 | −57.42 | 273.95 | 77.02 | 212.30 | 104.74 |
| 4 | 11.45 | 150.45 | 29.59 | 165.51 | 73.61 |
| 5 | 16.72 | 154.64 | 139.80 | 169.77 | 86.69 |
| 6 | −27.93 | 117.36 | 165.34 | 85.56 | 41.94 |
| Mean | −9.55 | 208.13 * | 95.55 * # | 172.25 * ^ | 84.62 * |
| Standard error | 18.5 | 31.2 | 20.5 | 21.1 | 10.8 |
| Standard deviation | 45.4 | 76.3 | 50.1 | 51.6 | 26.5 |

\* $p < 0.05$ group HM, BP, HM + BP, biphalin vs placebo group (one way ANOVA and Dunnett's method - all pairwise multiple comparison procedure)
\# $p < 0.05$ group HM vs group BP (t-test)
^ $p < 0.05$ group BP vs group HM + BP (t-test)

TABLE 9

Paw withdrawal test (right side)

| Rat | Placebo | HM | BP | HM + BP | Biphalin |
|---|---|---|---|---|---|
| 1 | 69.92 | 311.53 | 59.77 | 228.46 | 79.45 |
| 2 | −10.71 | 265.44 | 93.21 | 161.03 | 111.20 |
| 3 | −37.99 | 324.00 | 84.38 | 236.30 | 93.88 |
| 4 | −10.67 | −175.72 | 29.51 | 173.64 | 75.91 |
| 5 | 34.71 | 157.33 | 143.50 | 194.45 | 110.34 |
| 6 | −8.90 | 111.56 | 179.14 | 90.00 | 41.65 |
| Mean | 6.06 | 224.26 * | 98.25 * # | 180.65 * ^ | 85.40 * |
| Standard error | 15.9 | 36.0 | 22.4 | 21.8 | 10.6 |
| Standard deviation | 39.0 | 88.1 | 54.8 | 53.3 | 26.1 |

\* $p < 0.05$ group HM, BP, HM + BP, biphalin vs placebo group (one way ANOVA and Dunnett's method - all pairwise multiple comparison procedure)
\# $p < 0.05$ group HM vs group BP (t-test)
^ $p < 0.05$ group BP vs group HM + BP (t-test)
there is no statistically significant differences between average values of AUCs on the left and right side in each group For area under the curve (AUC) calculation the SigmaPlot v. 5.00 (SPSS Inc.) software was used (Area Under Curve Transform). This transform computes the area beneath a curve from X (time in days)) and Y (% MPE) data columns using the trapezoidal rule for unequally spaced X values. For statistical analysis of the data the SigmaStat statistical software (Jandel Corporation) was used.

EQUIVALENTS

From the foregoing detailed description of the specific embodiments of the invention, it should be apparent that a novel pain management regimen has been described. Although particular embodiments have been disclosed herein in detail, this has been done by way of example for purposes of illustration only. In particular, it is contemplated by the inventor that various substitutions, alterations, and modifications may be made to the invention without departing from the spirit and scope of the invention.

What is claimed is:

1. A drug a delivery device comprising a poly lactic-glycolic acid (PLGA) polymer carrier, said carrier consisting essentially of two drugs, wherein the first drug is an anesthetic agent and the second drug is an analgesic agent selected from the group consisting of an opioid and an opioid antagonist.

2. The device of claim 1, wherein said device is shaped to fit into a body cavity.

3. The device of claim 1, wherein said device is in the shape of a chest tube.

4. The device of claim 1, wherein said device is in the shape of a rod.

5. The device of claim 1, wherein said device is in the shape of a thread.

6. The device of claim 1, wherein said device is in the shape of a surgical drain.

7. The device of claim 1, wherein said device is in the shape of a catheter.

8. The device of claim 1, wherein said device is in the shape of a body cavity.

9. The device of claim 1, wherein a ratio of said first drug and said second drug is 50:50.

10. The device of claim 1, wherein said composition is at least 0.1% w/w of said device.

11. The device of claim 1, wherein said composition is at least 25% w/w of said device.

12. The device of claim 1, wherein said composition is at least 70% w/w of said device.

13. The device of claim 1, wherein said anesthetic agent is bupivacaine.

14. The device of claim 1, wherein said opioid is morphine or a morphine analog.

15. The device of claim 1, wherein said opioid is hydromorphone.

16. The device of claim 1, wherein said opioid agonist is biphalin.

17. The device of claim 1, wherein said polymer is biodegradable.

18. The device of claim 1, wherein said polymer is surface-erodible.

19. The device of claim 1, wherein said polymer is bulk-erodible.

20. The device of claim 1, wherein said device comprises a copolymer of lactic acid and glycolic acid at a ratio of 75:25 (PLGA-75:25).

21. The device of claim 1, wherein said device comprises a copolymer of lactic acid and glycolic acid at a ratio of 50:50 (PLGA-50:50).

22. The device of claim 1, wherein said device further comprises a buffering agent.

23. The device of claim 22, wherein said buffering agent is hydroxyapatite.

24. A method of continuously relieving pain in a subject, comprising implanting into said subject a drug delivery device comprising a poly lactic-glycolic acid (PLGA) polymer carrier, said carrier consisting essentially of two drugs, wherein the first drug is an anesthetic agent and the second drug is an analgesic agent selected from the group consisting of an opioid and an opioid antagonist, and wherein said device is placed parallel to a nerve.

25. The method of claim 24, wherein said nerve is a sciatic nerve.

26. The method of claim 24, wherein said device is implanted intrathecally.

27. The method of claim 24, wherein said subject is a human.

28. A method of continuously relieving pain in a subject, comprising implanting into said subject a drug delivery device comprising a poly lactic-glycolic acid (PLGA) polymer two drugs, wherein the first drug is an anesthetic agent and the second drug is an analgesic agent selected from the group consisting of an opioid and an opioid antagonist, and wherein said device is a thread and said implanting comprises surgically suturing a wound.

* * * * *

UNITED STATES PATENT AND TRADEMARK OFFICE
CERTIFICATE OF CORRECTION

| | | |
|---|---|---|
| PATENT NO. | : 6,913,760 B2 | Page 1 of 1 |
| APPLICATION NO. | : 10/213584 | |
| DATED | : July 5, 2005 | |
| INVENTOR(S) | : Daniel B. Carr et al. | |

It is certified that error appears in the above-identified patent and that said Letters Patent is hereby corrected as shown below:

Please insert the following paragraph at column 1, line 5:

--STATEMENT AS TO FEDERALLY SPONSORED RESEARCH

This invention was made with U.S. government support under the United States Department of Defense, Contract No. DAMD17-96-C-6043. The United States Government has certain rights in the invention.--

Signed and Sealed this

Twelfth Day of September, 2006

JON W. DUDAS
*Director of the United States Patent and Trademark Office*